United States Patent [19]

Belly et al.

[11] Patent Number: 5,045,477
[45] Date of Patent: * Sep. 3, 1991

[54] ANALYTICAL METHODS UTILIZING REDUCIBLE COMPOUNDS

[75] Inventors: Robert T. Belly, Webster; Albert J. Mura, Rochester; Theodore W. Esders, Webster; Brent A. Burdick, Rochester, all of N.Y.

[73] Assignee: Eastman Kodak Company, Rochester, N.Y.

[*] Notice: The portion of the term of this patent subsequent to May 24, 2005 has been disclaimed.

[21] Appl. No.: 344,870

[22] Filed: Apr. 28, 1989

Related U.S. Application Data

[60] Division of Ser. No. 824,766, Jan. 31, 1986, Pat. No. 4,857,271, continuation-in-part of Ser. No. 699,386, Feb. 7, 1985, abandoned.

[51] Int. Cl.$^5$ ............................................. G01N 21/00
[52] U.S. Cl. ..................................... 436/164; 422/56; 435/4; 436/172
[58] Field of Search .................................... 422/56–58; 436/164–174; 435/4

[56] References Cited

U.S. PATENT DOCUMENTS 3,980,479 9/1976 Fields et al. .
4,108,850 8/1978 Fields et al. .
4,139,379 2/1979 Chasman et al. .
4,144,306 3/1979 Figueras .
4,232,107 11/1980 Janssens .
4,307,188 12/1981 White .
4,371,604 2/1933 Van de Sande et al. .
4,746,607 5/1988 Mura et al. ........................ 422/56
4,803,160 2/1989 Wu ................................... 435/29
4,803,161 2/1989 Babb et al. ........................ 435/29

OTHER PUBLICATIONS

Van de Sande, *Agnew. Chem. Int. Ed. Engl.*, 22, pp. 191–209 (1983)

Primary Examiner—Robert J. Warden
Assistant Examiner—Timothy M. McMahon
Attorney, Agent, or Firm—J. Lanny Tucker

[57] ABSTRACT

Certain reducible compounds are useful in analytical compositions, elements and methods, e.g. for assays of bacterial cells. These compounds comprise a moiety which provides a detectable species (e.g. a dye) when released from the compound in an environment of pH 9 or less (i.e. physiological pH). Structurally, the reducible compounds are aromatic derivatives or quinones having suitable substituents which promote varying amounts of moiety release at physiological pH. When reduced at about pH 7, the preferred compounds release at least 50% of the available detectable species within 30 minutes.

8 Claims, 2 Drawing Sheets

ANALYTICAL METHODS UTILIZING REDUCIBLE COMPOUNDS

CROSS-REFERENCE TO RELATED APPLICATIONS

This is a divisional of Application Ser. No. 824,766, filed Jan. 31, 1986, now U.S. Pat. No. 4,857,271, and a continuation-in-part of U.S. Ser. No. 699,386, filed Feb. 7, 1985 now abandoned.

Reference is made to the following copending and commonly assigned applications:

U.S. Ser. No. 699,374 filed Feb. 7, 1985 by A. J. Mura et al and entitled USE OF SUBSTITUTED QUINONE ELECTRON TRANSFER AGENTS IN ANALYTICAL DETERMINATIONS, now U.S. Pat. No. 4,746,607.

U.S. Ser. No. 06/824,757, filed on even date herewith by Babb et al and entitled BIOLOGICAL AND ANALYTICAL USES OF PHENALENONE AND BENZPHENALENONE COMPOUNDS, now U.S. Pat. No. 4,803,161 and U.S. Ser. No. 06/824,755, filed on even date herewith by A. Wu and entitled USE OF POLYMERIC MORDANTS TO INCREASE THE INTENSITY OF RIGID FLUORESCENT DYES, now U.S. Pat. No. 4,803,160.

FIELD OF THE INVENTION

This invention relates to clinical chemistry. In particular, it relates to the use of reducible compounds in dry or wet assays of liquids, such as biological fluids, to release useful moieties or to detect living cells (e.g. bacteria) or other analytes. It also relates to novel compounds which can be reduced to provide a detectable species (e.g. a dye) at a pH of 9 or less.

BACKGROUND OF THE INVENTION

Chemical analysis of liquids, such as water, milk and biological fluids is often desirable or necessary for health maintenance and diagnostic care. Various compositions and elements to facilitate such analyses are known. Such compositions and elements generally include a reagent composition for determining a substance under analysis, identified as an "analyte" herein. The analyte can be a living organism or a nonlivie chemical substance. The reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of in-dwelling catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic bacteriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Current laboratory methods based on culturing microorganisms, e.g., the calibrated loop-direct streak method, require significant incubation periods (18-24 hours) before results can be determined. These laboratory methods are also time-consuming to perform and require considerable clinical training and facilities.

Known commercial methods for relatively rapid detection of bacteriuria have serious drawbacks. They are tedious, not completely reliable, require complex reagents or instrumentation, and have limited sensitivity to certain microorganisms and susceptibility to drug or other interferences. Hence, the usefulness of known methods is severely limited.

It is also known that bacterial microorganisms can reduce dyes, resulting in a colorless product (i.e. dye bleach). Alternatively, colorless materials, e.g. tetrazolium salts, can be reduced to form a colored formazan dye, as described in U.S. Pat. No. 3,415,718 (issued Dec. 10, 1968 to Forkman et al) and by Guze et al in *Am. J. Med. Sci.*, Dec., 1963, pp. 691–694. However, the use of formazan dyes for detecting microorganisms has several drawbacks. The formazan dyes generally have low extinction coefficients and therefore cannot be used to detect low levels of microorganisms. The tetrazolium salts have structures that are not readily modified to increase the extinction coefficients of the formazan dyes. Some formazan dyes are insoluble in water and can be toxic to the microorganisms.

U.S. Pat. No. 4,144,306 (issued Mar. 13, 1979 to Figueras) describes a multilayer element for analysis of liquids. This element can include an interactive composition which interacts with an analyte to release a preformed, detectable moiety from an immobile carrier nucleus upon oxidation or reduction. Such release generally requires the presence of a highly alkaline medium (i.e. pH greater than 13). The spectral absorption band of the preformed detectable moiety is the same before and after release. In other words, the detectable species is not shiftable from one spectral absorption band to another. Therefore, the reference teaches the use of radiation-blocking layers in the element to screen out unwanted absorption from unreleased detectable moiety during the assay.

U.S. Pat. Nos. 4,108,850 (issued Aug. 22, 1978 to Fields et al) and 4,139,379 (issued Feb. 13, 1979 to Chasman et al) describe ballasted electron-accepting nucleophilic displacement compounds (called BEND compounds therein) which can release dyes or other photographically useful fragments when reduced in the presence of silver halide, an incorporated reducing agent and an electron transfer agent. However, like the compounds described by Figueras, most of these BEND compounds release the desired moieties only in a high pH (13–14) environment. A few BEND compounds, e.g. those having reduction potentials at about −650 mV (in acetonitrile), will release dye at a lower pH. However, dye release from these compounds at low pH (i.e. less than about 9) is very inefficient, i.e. very slow, and would not provide a rapid clinical chemistry assay. BEND compounds that release dyes only at high pH cannot be used in analytical determinations which are generally carried out at physiological pH (i.e. <9). Highly alkaline conditions are undesirable for clinical analysis, and especially for detection of microorganisms because many key enzymes and organisms are inactivated at high pH. The BEND compounds which release dye at lower pH are unsuitable for analytical determinations because their dye release is too slow.

Hence, there is a need in the art for a rapid and highly quantitative assay for analytes or microorganisms in aqueous liquids which can be carried out at physiological pH.

SUMMARY OF THE INVENTION

The present invention overcomes the problems of the art with the use of certain reducible compounds. Therefore the present invention provides a composition buffered at a pH of 9 or less which comprises a reducible compound of the structure CAR$-(R^1)_n$ wherein CAR- is a substituted or unsubstituted aromatic or quinone nucleus, $R^1$ is a moiety which comprises a shiftable detectable species, and n is 1 or 2, provided the reducible compound is capable of being reduced at a pH of 9 or less to release the shiftable detectable species, and further provided that when $R^1$ is replaced with H, CAR$-(H)_n$ has an $E_{\frac{1}{2}}$ of either at least about +100 mV when measured in water, or of at least about −650 mV when measured in acetonitrile.

Also, a dry analytical element for the determination of an analyte comprises an absorbent carrier material and contains the reducible compound described above.

This invention also provides a method for the determination of an analyte. This method comprises the steps of:

A. at a pH of 9 or less, contacting a sample of a liquid suspected of containing an analyte with the reducible compound described above, and B. detecting the detectable species released as a result of the presence of the analyte.

This invention also provides a class of novel reducible intramolecular nucleophilic displacement, or RIND, compounds of the structure CAR-$R^1$ wherein CAR- is

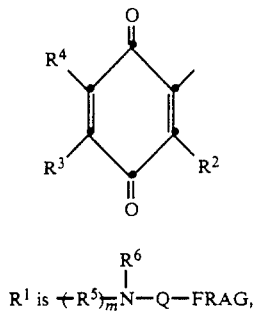

$R^1$ is $+R^5)_{\overline{m}}N-Q-$FRAG, $R^2$ and $R^4$ are independently hydrogen, substituted or unsubstituted alkyl, substituted or unsubstituted aryl or an electron withdrawing group, $R^3$ is $R^1$, hydrogen, substituted or unsubstituted alkyl, substituted or unsubstituted aryl or an electron withdrawing group, or $R^3$ and $R^4$, taken together, represent the atoms necessary to complete a substituted or unsubstituted fused carbocyclic ring, $R^5$ is substituted or unsubstituted alkylene of 1 or 2 carbon atoms, $R^6$ is substituted or unsubstituted alkyl, substituted or unsubstituted aryl, substituted or unsubstituted cycloalkyl or substituted or unsubstituted heterocycle, provided that when FRAG is a fluorogen, $R^6$ is methyl, Q is carbonyl or thiocarbonyl, FRAG is a shiftable detectable species which provides a detectable species when released from the reducible compound, and m is 0 or 1, provided that when $R^1$ is replaced by H, CAR- H has an $E_{\frac{1}{2}}$ of either at least about +100 mV when measured in water, or of at least about −650 mV when measured in acetonitrile.

The present invention provides a means for using reducible compounds in rapid and highly quantitative determinations of analytes, e.g. enzymes, metabolites or living cells (e.g. bacterial microorganisms) in liquids conducted at physiological pH (i.e. 9 or less). It also provides a class of novel compounds particularly useful in such determinations. Further, it also provides a means for releasing chemically or biologically useful moieties which can be converted into detectable species.

The present invention overcomes many of the drawbacks of known analytical compositions and elements. In particular, the reducible compounds described herein, upon reduction, will efficiently provide a detectable species (e.g. a chromogen or fluorogen) at physiological pH, thereby avoiding the problems encountered at high pH. For example, when the preferred compounds of this invention are reduced at about pH 7 at least 50% of the available detectable species is released within 30 minutes. Further, in a preferred embodiment, the chromogens and fluorogens which can be released from these compounds have high extinction coefficients, thus providing improved sensitivity, for example, to detect low levels of bacteria or other analytes present in low concentrations.

It is also an advantage of this invention that the measured spectral absorption band of the released detectable species is different from the spectral absorption band of the reducible compound. Hence, radiation-blocking layers are unnecessary in the element to screen out unwanted absorption from unreleased species, and the determination can be made with a single layer analytical element.

DETAILED DESCRIPTION OF THE INVENTION

Figure 2:
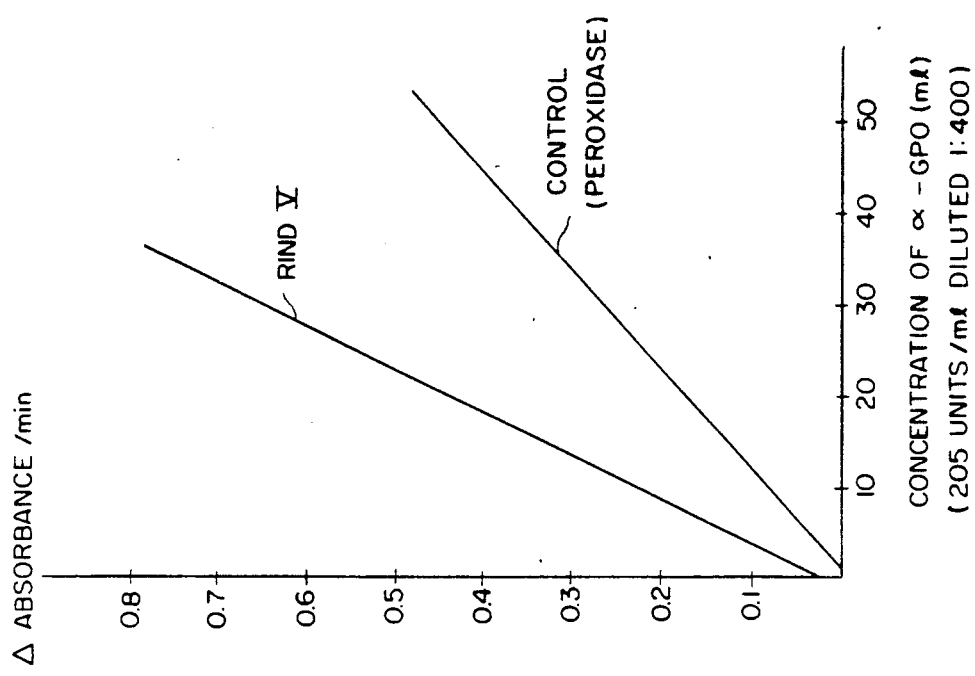
FIG. 2 is a graphical plot of the change in absorbance/min. vs. concentration of $\alpha$-glycerophosphate oxidase for both a state of the art assay and the assay of this invention in reference to Example 8 below.

The reducible compounds useful in the practice of this invention are broadly defined as organic compounds containing a shiftable detectable species which can be reduced at physiological pH (i.e. 9 or less) to release the shiftable detectable species. The term "shiftable" is defined as: (1) a chromogen moiety, which has a first spectral absorption band while attached to the reducible compound and a second spectral absorption band when released, or a fluorogen moiety which has first spectral absorption and emission bands while attached and second spectral absorption and emission bands when released, (2) a chemically or biologically useful moiety which is inactive, blocked or otherwise inaccessible when attached to the reducible compound but active, unblocked or accessible when released, or (3) a chemically or biologically useful moiety which is active or accessible when attached to the reducible compound but inactive or otherwise inaccessible when released.

Thus, a shiftable detectable species is a moiety which has a first spectral absorption band while attached to the reducible compound before reduction and release, but which exhibits a second spectral absorption band during analytical measurement. The detectable species is chemically modified when attached to the reducible compound nucleus so that the spectral absorption band of the reducible compound is "shifted" from the band that the species has when released. Generally, but not necessarily, the band is relocated to substantially shorter wavelengths when the species is a part of the reducible compound. In all cases, the two bands do not overlap to a significant extent. The change (i.e. "shift") from one spectral absorption band to another can be due to the mere release of the moiety from the reducible compound, or alternatively, it can be caused by such release coupled with either interaction of the released moiety with metal ions or a mordant, or coupled with a change in the assay environment (e.g. change in pH). Any such change in the environment must still keep the pH at 9 or less.

As noted above, shiftable detectable species can also be a chemically or biologically useful moiety which, when attached to the reducible compound, is inactive or blocked or otherwise inaccessible, but when released at physiological pH becomes biologically or chemically active or accessible for further interaction. The released, active species can be detectable itself or is capable of one or more subsequent chemical, physical or biological reactions to provide a detectable species. The method of this invention provides a means for releasing such moieties, e.g. electron transfer agents, enzymes, enzyme substrates, enzymes inhibitors, cofactors, catalysts, reactants, etc. upon reduction of the reducible compound, preferably at physiological pH, for a variety of chemical or biological purposes.

Further, a shiftable detectable species can be a chemically or biologically useful moiety which, when attached to the reducible compound, is active, or otherwise accessible for one or more subsequent chemical, physical or biological reactions, but when released at physiological pH becomes inactive or otherwise inaccessible for such reactions.

More particularly, the compounds useful in this invention have the structure CAR$-(R^1)_n$ wherein CAR- represents a substituted or unsubstituted aromatic or quinone nucleus, $R^1$ is a moiety comprising a shiftable detectable species defined below, and n is 1 or 2. Examples of such nuclei are presented below. Further, when $R^1$ is replaced by H, CAR$-(H)_n$ has a reduction potential ($E_{\frac{1}{2}}$) of either at least about +100 mV when measured in water, or of at least about −650 mV when measured in acetonitrile. This $E_{\frac{1}{2}}$ value facilitates the reduction and subsequent release of the shiftable detectable species from the compound at physiological pH (i.e. 9 or less). Such measurements are made according to standard electrochemical techniques using either differential pulse polarography or cyclic voltametry (see, e.g. Sawyer and Roberts, Jr., *Experimental Electrochemistry for Chemists*, John Wiley & Sons, New York, 1974). Preferably, the $E_{\frac{1}{2}}$ is from about +100 mV to about +400 mV as measured in water, or from about −650 to about −300 mV as measured in acetonitrile. Both ranges are given because some of the reducible compounds are best measured in water whereas others are best measured in acetonitrile. Further details of measuring the $E_{\frac{1}{2}}$ are described below prior to Table I. The desired $E_{\frac{1}{2}}$ is achieved by appropriate electron withdrawing groups on the CAR- nucleus, or by a combination of a fused ring attached to the nucleus and electron withdrawing groups.

Examples of useful reducible compounds are illustrated below without intending to limit this invention.

In one embodiment, the reducible compounds can be reduced to provide a detectable species through quinonemethide formation, similar to the description by Van de Sande in *Angew. Chem. Int. Ed. Engl.* 22, pp. 191–209 (1983) and U.S. Pat. No. 4,232,107 (issued Nov. 4, 1980 to Janssens), but which have the desired $E_{\frac{1}{2}}$ properties.

In another embodiment, useful reducible compounds include sulfilimides and sulfenylsulfonamides similar to those described on page 206 of the Van de Sande reference noted above, but which have the desired $E_{\frac{1}{2}}$ properties.

In a preferred embodiment, the reducible compounds of this invention are RIND compounds, i.e. reducible compounds capable of undergoing intramolecular nucleophilic displacement at physiological pH to release one or more shiftable detectable species when a nucleophilic group is generated by at least a one electron reduction of the compound. In other words, such displacement occurs when the RIND compound is reduced by a suitable reductant which provides the necessary electrons (described in more detail below). The distinction of these RIND compounds over the many similar benzoquinone compounds used in the photographic art is that the RIND compounds have a higher $E_{\frac{1}{2}}$ value, thereby facilitating their reduction and subsequent release of a shiftable detectable species (e.g. a dye) at physiological pH (i.e. 9 or less). This release is very efficient in that, for most of the preferred compounds, at least 50% of the detectable species is provided within 30 minutes at about pH 7. These RIND compounds are particularly useful because they release the detectable species rapidly, allowing for a rapid assay. Similar photographic compounds have lower $E_{\frac{1}{2}}$ values and either release dye only at high pH (13–14), or release dye very inefficiently (i.e. slowly) at physiological pH. Such compounds are described in U.S. Pat. No. 4,144,306 (noted above). When a RIND compound of this invention is reduced, e.g. in a clinical chemistry assay, the shiftable detectable species is released and diffuses throughout a solution, or within the layers of an analytical element efficiently (i.e. quickly).

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

The rate of nucleophilic displacement is substantially zero prior to reduction of the RIND compound. Hence, the RIND compounds are stable prior to that reduction.

Particularly useful RIND compounds are those of a novel class of reducible compounds which have the structure CAR-$R^1$ wherein CAR— is

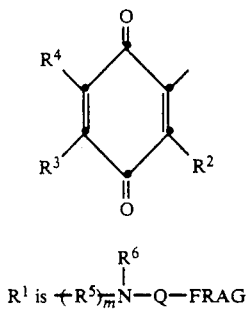

$R^1$ is $+R^5)_{\overline{m}}N-Q-FRAG$ wherein m is 0 or 1, and preferably 1. $R^5$ is substituted or unsubstituted alkylene, preferably of 1 or 2 carbon atoms in the backbone (e.g. methylene, ethylene, alkoxymethylene, etc.). Most preferably, $R^5$ is methylene. Q is carbonyl or thiocarbonyl and preferably carbonyl.

$R^6$ is substituted or unsubstituted alkyl preferably of 1 to 40 carbon atoms (e.g. methyl, ethyl, n-propyl, isopropyl, t-butyl, hexyl, decyl, lauryl, benzyl, etc.), substituted or unsubstituted cycloalkyl preferably of 4 to 40 carbon atoms (e.g. cyclobutyl, cyclohexyl, 4-methylcyclohexyl, etc.), substituted or unsubstituted heterocycle preferably of 5 to 40 atoms (carbon and heteroatoms, e.g. pyridyl, etc.), or substituted or unsubstituted aryl of 6 to 40 carbon atoms (e.g. phenyl, xylyl, naphthyl, p-nitrophenyl, anthryl, p-t-butoxyphenyl, etc.). Preferably, $R^6$ is lower alkyl of 1 to 3 carbon atoms (substituted or unsubstituted). However, when FRAG is a fluorogen, $R^6$ is methyl.

FRAG is a shiftable detectable species as defined above. Preferable, along with the remainder of the molecule, it has a first spectral band(s), but when it is cleaved from the RIND compound, it provides a detectable species having a second spectral band(s), as described above. This species is released in an amount which can be directly related to the amount of reductant present. The specific composition of FRAG can vary considerably depending upon the type of detectable species desired and upon the particular detection means employed.

The shiftable detectable species can be a material which is directly detectable by a suitable means, as well as a material which can react with other substances, e.g. analytes, enzymes or other reagents to provide a detectable species. Such species include those detectable by radiometric means, including chromogens (e.g. dyes or pigments) which can be detected colorimetrically and fluorogens (e.g. fluoroscent dyes or probes) which can be detected fluorometrically. Additionally, the detectable species can be a phosphorescent species, a chemiluminescent species, or any other detectable species known to one skilled in the art.

Particularly useful shiftable detectable moieties are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenone and benzphenalenone, fluorescein and rhodamine fluorescent dyes, and others known in the art. Phenalenone dyes are particularly useful.

Useful phosphorescent species include such phosphors as 2',5'-dibromofluorescein and 4',5'-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno, and most preferably it is oxy. However, when FRAG is a fluorogen, the linkage is oxy or thio.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, benzyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined hereinabove) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecule.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

The RIND compounds of this invention readily release FRAG at physiological pH. Preferred compounds release the shiftable detectable species at about pH 7 so quickly that at least about 50% of the available species is released in 30 minutes. Most preferably, at least about 75% is released within that time.

Representative novel and preferred RIND compounds of this invention are listed in Table I below in reference to the following structure:

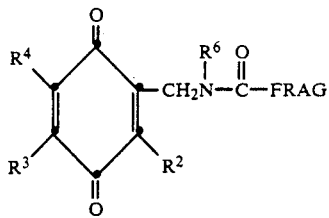

The $E_{\frac{1}{2}}$ values in Table I were determined for the quinone nucleus of this structure having a hydrogen atom in place of

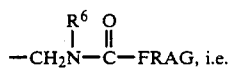

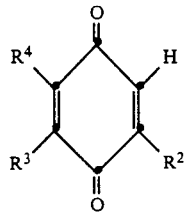

The $E_{\frac{1}{2}}$ values (where available) were measured in an aqueous emulsion of the quinone dissolved in N,N-dimethylformamide, a nonionic surfactant (TRITON X-100) and sodium phosphate buffer (pH 7). A normal hydrogen electrode was used as a standard. Some $E_{\frac{1}{2}}$ values (denoted by *) were measured in acetonitrile using a saturated calomel electrode as a standard. $E_{\frac{1}{2}}$ values not available are denoted by "NA".

TABLE I

| RIND Compound | R⁶ | R² | R⁴ | R³ | FRAG | FRAG | $E_{\frac{1}{2}}(mV)$ |
|---|---|---|---|---|---|---|---|
| I. | —CH₃ | —CH(CH₃)—C₆H₄—SO₂NHC₁₀H₂₁ | same as R² | —CH₂N(CH₃)—C(=O)— | naphthalene with —O⁻ | —N=N—C₆H₃(SO₂CH₃)(NO₂); —NHSO₂—C₆H₄—SO₂NH₂ | −528* |
| II. | —CH₃ | —CH(CH₃)—C₆H₄—NO₂ | same as R² | " | " | " | +236 |
| III. | —CH₃ | —CH(CH₃)—C₆H₄—SO₂NHCH(CH₃)₂ | same as R² | " | " | " | NA |
| IV. | —CH₃ | —C₆H₅ | same as R² | " | " | " | −460* |
| V. | —CH₃ | —C₆H₄—NO₂ | R³ and R⁴ together form cyclohexane ring | | " | " | +214 |
| VI. | —CH₃ | —C₆H₅ | " | | " | " | +180 |

TABLE I-continued

| RIND Compound | R⁶ | R² | R⁴ | R³ | FRAG | E₁(mV) |
|---|---|---|---|---|---|---|
| VII. | —CH₃ | 4-NO₂-phenyl | " | " | " | +236 |
| VIII. | —CH₃ | 4-SO₂NHCH(CH₃)₂-phenyl | " | " | " | +212 |
| IX. | —CH₃ | 4-CN-phenyl | " | " | " | +220 |
| X. | —CH₃ | 4-OCH₃-phenyl | " | " | " | +154 |
| XI. | —CH₃ | 3,5-(NO₂)₂-phenyl | " | " | " | +186 |
| XII. | —CH₃ | 4-C(O)C₁₀H₂₁-phenyl | " | " | " | +206 |
| XIII. | —CH₃ | 4-C(O)CH₃-phenyl | " | " | " | +212 |

TABLE I-continued

| RIND Compound | R⁶ | R² | R⁴ | R³ | FRAG | $E_j$(mV) |
|---|---|---|---|---|---|---|
| XIV. | —CH₃ | 4-Br-phenyl | " | | " | +192 |
| XV. | —CH₃ | —H | " | | " | +213 |
| XVI. | —C₁₂H₂₅ | 4-CN-phenyl | " | | " | +220 |
| XVII. | —CH₃ | " | R³ and R⁴ together form (ring) | | " | +240 |
| XVIII. | —CH₃ | 4-NO₂-phenyl | t-butyl | —H | " | NA |
| XIX. | —CH₃ | 4-methylphenyl | R³ and R⁴ together form (ring) | | " | +242 |
| XX. | —CH₃ | " | R³ and R⁴ together form (ring) | | " | +222 |

TABLE I-continued

| RIND Compound | R⁶ | R² | R⁴ | R³ | FRAG | E½(mV) |
|---|---|---|---|---|---|---|
| XXI. | —CH₃ | [4-(1-methylethyl)phenyl-SO₂NHC₁₀H₂₁] | same as R² | [—CH₂N(CH₃)C(O)—] | [naphthalene with —O⁻, N=N-phenyl-SO₂NH₂, NHSO₂CH₃ substituents] FRAG | |
| XXII. | —CH₃ | " | " | " | [methyl-substituted phenyl with CH₃ group and lactone ring] | NA |
| XXIII. | —CH₃ | [3-nitrophenyl] | R³ and R⁴ together form [ring structure] | | [naphthalene with —O⁻, N=N-phenyl-SO₂CH₃, NO₂, NHSO₂ substituents] | +214 |
| XXIV. | —CH₃ | [2,5-dichlorophenyl] | R³ and R⁴ together form [ring structure] | | [naphthalene with —O⁻, N=N-phenyl-NO₂, SO₂CH₃, NHSO₂-phenyl-SO₂NH₂ substituents] | +236 |

TABLE I-continued

| RIND Compound | R[6] | R[2] | R[4] | R[3] | FRAG | $E_{\frac{1}{2}}$(mV) |
|---|---|---|---|---|---|---|
| XXV. | —CH₃ | -phenyl | R[3] and R[4] together form ⟨C₁₂H₂₅⟩ | | same as for XXIV | +222 |
| XXVI. | —CH₃ | " | —CH₃ | —CH₃ | " | +144 |
| XXVII. | —CH₃ | " | R[3] and R[4] together form CH₃-CH-CH₂-CH-CH₃ with CH₃ | | " | +122 |
| XXVIII. | —CH₃ | " | (CH₃)₂HC-CH-CH₃ | R[3] and R[4] together form | " | +174 |
| XXIX. | —CH₃ | phenyl-CN | R[3] and R[4] together form | | " | +220 |
| XXX. | —CH₃ | phenyl | R[3] and R[4] together form | | (pyrene derivative with =O and —O— substituents) | +222 |

TABLE I-continued

| RIND Compound | R⁶ | R² | R⁴ | R³ | FRAG | E₁(mV) |
|---|---|---|---|---|---|---|
| XXXI. | —CH₃ | (2,4-dichlorophenyl) | | | " | +236 |
| XXXII. | —CH₃ | (2-nitrophenyl) | R³ and R⁴ together form (ring) | | | +214 |
| XXXIII. | —CH₃ | (3-nitrophenyl) | " | | " | +236 |
| XXXIV. | —CH₃ | (4-SO₂NH(CH₃)₂-phenyl) | " | | " | +212 |

RIND compounds V, VII, VIII, IX, XX, XXIV, XXIX, XXX and XXXI are preferred in the practice of this invention with XXIX and XXXI being most preferred.

The novel RIND compounds of this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of the carbamoyl chloride with the FRAG moiety. Representative preparations are provided in Examples 1, 17, 21 and 22 below.

Other RIND compounds useful in the practice of this invention include those having the appropriate $E_{\frac{1}{2}}$ values and the structure CAR—$(R^1)_n$ wherein:

(1) CAR- is a substituted or unsubstituted nucleus of a 1,2-naphthoquinone, 1,2, -, 1,4- or 9,10-anthraquinone, 4,4′-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$. $R^1$ is

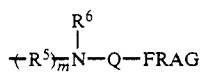

as defined above, and n is an integer of 1 or 2.

(2) CAR— is

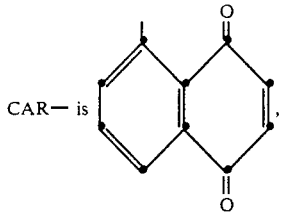

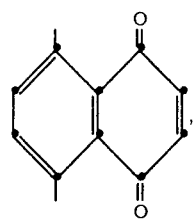

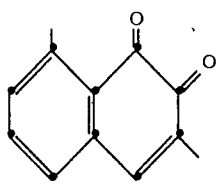

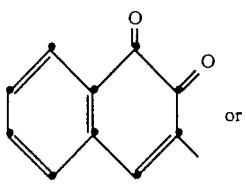

or

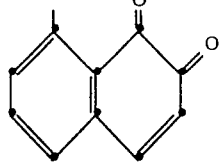

any of which can be substituted with one or more electron withdrawing groups as described above for $R^2$, $R^3$ and $R^4$. $R^1$ is

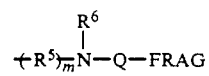

as defined above, and n is 1 or 2.

(3) CAR- is a substituted or unsubstituted nitrobenzenoid nucleus of the structure

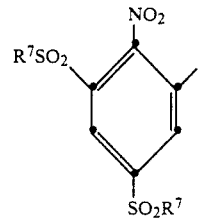

wherein $R^7$ is substituted or unsubstituted alkyl of 1 to 20 carbon atoms (e.g. methyl, ethyl, methoxymethyl, isopropyl, dodecyl, hexadecyl, octadecyl, etc.), and $R^1$ is

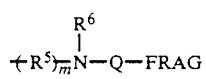

as defined above and n is 1. These compounds are similar to some described in U.S. Pat. No. 4,139,379 (noted above).

All of these reducible compounds can be prepared using techniques and starting materials known in the art or readily apparent to a skilled synthetic chemist. See, e.g. Examples 19 and 20 below.

Generally, the reducible compounds described herein have limited water solubility. Hence, it is best, when using them in an aqueous environment, to prepare a dispersion of the compound prior to use, e.g. in a coating formulation. Such dispersions generally comprise the reducible compound, an aqueous buffer solution and either a water-solubilizing surfactant or a water-miscible organic solvent for the compound, or both.

Surfactants which are useful in the practice of this invention include any surfactants which do not inhibit compound reduction. Generally, for detection of living cells, the useful surfactants are nonionic surfactants, including, for example, alkylarylpolyethoxy alcohols (e.g. TRITON X-100 and X-305 available from Rohm & Haas, Philadelphia, Pa., U.S.A.), p-alkylaryloxypolyglycidols (e.g. SURFACTANT 10G available from Olin Corp., Stamford, Conn., U.S.A.), TWEEN 80 (available from ICI Americas, Inc., Wilmington, Del., U.S.A.), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular reducible compound can be readily determined by routine experimentation.

A dispersion can be prepared in the following general manner with the particular details of such a preparation illustrated in Example 2 below. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of dispersion. This preparation is generally carried out at room temperature.

These dispersions generally contain a buffer in an amount effective to maintain a physiological pH (9 or less). The concentration of buffer in the dispersion can vary widely, but is generally from about 0.01 to about 0.1 molar. Representative buffers include phosphates, borates and others reported by Good et al in *Biochemistry*, 5, 467 (1966), and *Anal. Biochem.*, 104, 300 (1980).

The reducible compounds described herein are useful in compositions for analytical determination (i.e. qualitative or quantitative detection) of aqueous and nonaqueous liquids, e.g. biological fluids, manufacturing processes, wastewater, food stuffs, etc. Determinations can be made of various analytes via a single reaction or a sequence of reactions which bring about reduction of the compound and release of the moiety. The various analytes include living cells (e.g. bacteria, white blood cells, yeast, fungi, etc.), enzymes (e.g. lipase, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH-based, FADH-based or oxidase-based assays), biological or chemical reductants other than living cells which will reduce the reducible compound (e.g. ascorbates, cysteine, glutathione, thioredoxin, etc.), metabolizable substances (e.g. glucose, lactic acid, triglycerides, cholesterol, etc.), immunoreactant (e.g. antigens, antibodies, haptens, etc.).

The compositions can be used to monitor enzyme redox reactions as well as flavin adenine dinucleotide (FAD-FADH)-based and nicotinamide adenine dinucleotide (NAD-NADH)-based and (NADP-NADPH)-based reactions. In such instances, the reducible compound can be used to provide a detectable species in place of NADH.

The reducible compounds described herein, and especially the novel RIND compounds of this invention, are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, white blood cells, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

When determining living cells using the reducible compounds, it is preferable for rapid dye release in such determinations that the living cells interact with an electron transfer agent (herein ETA). The presence of an ETA may also provide more efficient dye release for analytical determinations of nonliving analytes. The ETA is a mobile compound which acts as an intermediary between the substance being determined (e.g. living cell) and the reducible compound.

In general, the ETA compounds useful in the practice of this invention have an $E_{\frac{1}{2}}$ in the range of from about $-320$ to about $+400$ mV as measured in aqueous buffer (pH 7) versus the normal hydrogen electrode using a differential pulse polarographic technique with a PAR Potentiostat (Princeton Applied Research, Princeton, N.J.). In general, the potential of the ETA should be more positive than the potential of the substance to be determined (i.e. analyte) and less positive than the potential of the RIND compound. That is, the ETA should be more easily reduced than the analyte and less easily reduced than the reducible compound. They are generally present at a concentration that is dependant upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds useful in the practice of this invention which provide further advantages of low background are those which are the subject of U.S. Ser. No. 699,374 of Mura et al noted above. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone. The most preferred ETAs are those designated as I, III, IV, XXVI and XXVII of Table I of the Mura et al application.

The detection of living cells, and particularly of bacterial cells, is often carried out in the presence of a nutrient for those cells although its presence is not essential. Any nutrient media can be used which contains useful carbon, and optionally nitrogen, sources. Suitable nutrient media having proper components and pH are well known in the art. Particularly useful nutrients are glucose or tryptose alone or in combination.

The present invention is adaptable to either solution or dry assays. In a solution assay, a solution (or dispersion) containing a reducible compound, and preferably an ETA, is prepared and contacted with a liquid test sample containing the living cells or analyte to be determined by mixing. The ETA can also be mixed with the test sample prior to mixing with the reducible compound. Generally the reducible compound is mixed with the test sample in a suitable container (e.g. test tube, petrie dish beaker, cuvette, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the detectable species, for example, at a wavelength in the spectral absorption band of the chromogen species, or at a wavelength in the emission band of the fluorogen species which band is different than the band the reducible compound had prior to species release. Such an evaluation can be done with suitable detection equipment.

A solution assay can also be carried out by contacting a porous, absorbent material, e.g. paper strip, containing the test sample with a dispersion of the reducible compound. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Other reagents can be present in amounts readily determined by one skilled in the art.

Alternatively, the method of this invention can be practiced in a dry assay with a dry analytical element. Such an element can be a absorbent carrier material, i.e. a thin sheet or strip of self-supporting absorbent or bibulous material, such as filter paper or strips, which contains the reducible compound or a dried residue of the dispersion comprising same. Such elements are known in the art as test strips, diagnostic elements, dip sticks, diagnostic agents and the like.

When employed in dry analytical elements, the reducible compounds described herein can be incorporated into a suitable absorbent carrier material by imbibition or impregnation, or can be coated on a suitable absorbent carrier material. Alternatively, they can be added to the element during an assay. Useful carrier materials are insoluble and maintain their structural integrity when exposed to water or biological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Patent No. 2,052,057 (published Jan. 21, 1981).

A dry assay can be practiced to particular advantage with an analytical element comprising a nonporous support having thereon at least one porous spreading zone as the absorbent carrier material. The reducible compound can be in the spreading zone or in a different zone (e.g. reagent zone, registration zone, hydrophilic zone, etc.). The spreading zone can be prepared from any suitable fibrous or non-fibrous material or mixtures of either or both. The void volume and average pore size of this zone can be varied depending upon the use intended. For example, if whole blood or other liquid samples containing cells or high molecular weight materials are to be assayed, the void volume and average pore size are generally greater than if serum or urine is to be assayed.

The spreading zone can be prepared using fibrous materials, either mixed with a suitable binder material or woven into a fabric, as described in U.S. Pat. No. 4,292,272 (issued Sept. 29, 1981 to Kitajima et al), from polymeric compositions (e.g. blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

The dry analytical element of this invention can be a single self-supporting porous spreading zone containing a reducible compound and any other desired reagents for a particular use, but preferably such zone is carried on a suitable nonporous support. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection (reflection, fluorescence or transmission spectroscopy) and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be in a single coated layer. Besides the patents noted above, suitable element formats and components are described also, for example, in U.S. Pat. Nos. 4,042,335 (issued Aug. 16, 1977 to Clément) and 4,144,306 (noted above) and Re. 30,267 (reissued May 6, 1980 to Bruschi).

In the elements of this invention, the amount of the reducible compound can be varied widely, but it is generally present in a coverage of at least about 0.01, and preferably from about 0.05 to about 0.2, $g/m^2$. Optional, but preferred reagents (e.g. ETA, nutrient, buffer, etc.) are generally present in the following coverages:

ETA: generally at least about 0.001, and preferably from about 0.01 to about 1, $g/m^2$, nutrient: generally at least about 0.05, and preferably from about 0.1 to about 2, $g/m^2$ (used only in living cell detection), buffer (pH≦9): generally at least about 0.1, and preferably from about 0.5 to about 2, $g/m^2$, and surfactant: generally at least about 0.1, and preferably from about 0.2 to about 5, $g/m^2$.

One or more of the zones can contain a variety of other desirable, but optional, components, including activators, binders (generally hydrophilic), antioxidants, coupler solvents, etc. as is known in the art, as well as any reagents needed for assay of a particular analyte.

In one embodiment of this invention, an element for detection of microorganisms (e.g. yeast, fungi, bacteria, etc.) in an aqueous liquid comprises an electron transfer agent and a reducible compound, both of which are described above. It is desirable that these elements also contain a nutrient for the living cells and a buffer which maintains physiological pH during the assay (e.g. when contacted with a 1–200 μl sample of test liquid). Such an element can be used to detect bacteria, for example, in a urine sample (e.g. one pretreated to eliminate reductive interferents) by physically contacting the sample and element in a suitable manner, and detecting the detectable species released from the reducible compound as a result of the presence of the bacteria at the appropriate wavelength.

Representative elements and their use to detect bacteria are described in Examples 3, 5, 6, 11–14 and 25 below.

In another embodiment of this invention, an element is used for the determination of a nonliving biological or chemical analyte in an aqueous liquid. An interactive composition containing one or more reagents can be incorporated into the element or added at the time of the assay. Examples of such analytes are described above. The amount of detectable species detected can be correlated to the amount of analyte present in the liquid sample.

The element of this invention is also useful for determining other reductants such as ascorbate (ascorbic acid and equivalent alkali metal salts), cysteine, glutathione, thioredoxin and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (e.g. 1–200 μl) of the liquid to be tested so that the sample mixes with the reagents in the element. Such contact can be accomplished in any suitable manner, e.g. dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the reducible compound is reduced releasing a species which can be detected in a suitable manner. Preferably, as noted above, the detectable species is a colorimetric dye or fluorescent dye which can be detected with conventional colorimetric or fluorometric apparatus and detection procedures. If the detectable species is other than a chromogen or fluorogen, for example, a chemiluminescent or phosphorescent moiety, suitable chemiluminescence or phosphorescence detecting means can be employed. Spectral determinations can be made either at the maximum wavelength of the dye or at wavelengths other than the maximum wavelength.

Reagents used in the following examples were obtained as follows: lactate dehydrogenase, peroxidase, D,L-α-glycerophosphate, nicotinamide adenine dinucleotide, reduced form (NADH), glucose oxidase, ascorbic acid, sodium salt and phenazine methosulfate from Sigma Chemical Co. (St. Louis, Mo., U.S.A.), brain heart infusion (BHI) and tryptose nutrient media from Difco Labs (Detroit, Mich., U.S.A.), TRITON X-100 surfactant from Rohm & Haas (Philadelphia, Pa., U.S.A.), BRIJ 35 surfactant from ICI Americas, Inc. (Wilmington, Del., U.S.A.), ZONYL FSN surfactant from DuPont Co. (Wilmington, Del., U.S.A.), and the bacterial microorganisms from the American Type Culture Collection (ATCC) in Rockville, Md., U.S.A. All other reagents were either obtained from Eastman Organic Chemicals (Rochester, N.Y., U.S.A.) or prepared using known starting materials and procedures.

*Escherichia coli* (ATCC 25922) cells were grown in BHI medium at 37° C. without shaking and transferred daily. Forty ml of the cells grown overnight were harvested by centrifugation and resuspended in 10 ml of a 0.05 molar potassium phosphate buffer (pH 7.5). Solution 1 was prepared by adding 5 ml of the cell suspension to 9 ml of buffer. Solution 2 was prepared by adding 1 ml of solution 1 to 9 ml of buffer. Solutions 2a, 2b, 2c, etc. were prepared by a 1:1 dilution of Solution 2. The turbidity of each solution was measured at 620 nm against a buffer blank in a commercially available Beckman A25 spectrophotometer. A linear relationship between turbidity measurement and viable cell counts had been predetermined. An absorbance of 0.1 was found to be equivalent to about $6 \times 10^7$ *E. coli* cells/ml. Using this relationship and the known dilution factor, the number of cells in Solution 1 was determined.

In the preparation of the illustrated reducible compounds, the identity and purity of the intermediates were determined by infrared (IR) spectra as measured in a commercially available Perkin-Elmer 137 spectrophotometer [sharp(s) or broad(b) bands yielding structural information are reported in reciprocal centimeters ($cm^{-1}$)] or by nuclear magnetic resonance (NMR) spectra measured in a conventional Varian T60 NMR spectrophotometer [chemical shifts reported in δ values in ppm to tetramethylsilane at broad(b), singlet(s), multiplet(m) or broad singlets(bs) peaks]. The identity and purity of final products were determined by IR, NMR spectroscopy and elemental analysis.

The following examples are presented to illustrate the practice of this invention. The identified RIND compounds are the reducible compounds included in Table I above.

EXAMPLE 1

Preparation of RIND VII Compound

Step 1

A mixture of p-nitroaniline (27.6 g, 0.199 mole), concentrated HCl (80 ml) and water (200 ml) was warmed until solution was obtained, then cooled to 0°–5° C. Sodium nitrite (13.8 g, 0.2 mole), dissolved in $H_2O$ (25 ml), was added slowly to prevent any rise in temperature. After stirring at 0° C. for one hour, the resulting diazonium salt was added slowly to a mechanically stirred mixture of p-benzoquinone (25.9 g, 0.23 mole), sodium acetate (100 g, 1.2 mole), and ice water (2300 ml) in a 4 liter beaker. The golden colored heterogeneous mixture was stirred in an ice bath for four hours and slowly warmed to room temperature. The solid was isolated by filtration, washed repeatedly with water, then dried to afford 44.4 g (97% yield) of intermediate A of sufficient purity for use in the next step. The product could be recrystallized from 2:1/EtOH:acetone. NMR ($CDCl_3$/DMSO-$d_6$), δ7 (b, quinone H's), 7.6–8.6 (AA'XX'-phenyl).

Step 2a

A mixture of intermediate A (50 g, 0.218 mole), 1,3-cyclohexadiene (20.9 g, 0.26 mole) and methylene chloride (250 ml) was heated at reflux overnight under nitrogen. The solvent was removed and the crude protohydroquinone was used immediately in the next step.

Step 2b

Rearrangement of the protohydroquinone was carried out by adding KHCO$_3$ (42 g, 0.42 mole) and MeOH (400 ml), and heating to reflux for 30 minutes under nitrogen. The mixture was cooled, filtered and the filtrate was poured into dilute HCl/ice water. Filtration and drying (vacuum oven at 50° C.) afforded 64 g of crude intermediate B, sufficiently pure for use in the next step. NMR (CDCl$_3$), $\delta$1.5 (s, —CH$_2$CH$_2$—), 4.5 (b, ring junction H's), 6.6 (m, —CH=CH—), 6.7 (s, HQ-H), 7.7–8.4 (AA'XX', phenyl H's).

Step 3

Intermediate B (22.8 g, 73 mmole) was dissolved in tetrahydrofuran (THF) (750 ml) in a Parr shaker bottle, and 10% palladium on carbon catalyst was added under a nitrogen atmosphere. This mixture was placed on a commercial Parr shaker apparatus under 40 psi (2.75 bars) of hydrogen and shaken for 10–11 minutes. The reaction mixture was then filtered under a nitrogen atmosphere and the solvent removed under vacuum to give intermediate C as an orange semisolid. Recrystallization from methylene chloride gave 12.8 g (56% yield) of pure intermediate C as an orange solid. NMR (CDCl$_3$), $\delta$, 1.6 (m, CH$_2$CH$_2$), 3.4 (bs, —CH), 8 (AA'XX', nitrophenyl H's).

Step 4

A mixture of intermediate C (3.5 g, 11.2 mmole), N,N(diisobutoxymethylene)methylamine (4.5 g, 22.4 mmole) and toluene (15 ml) was heated overnight at 115° C. under nitrogen. A stream of nitrogen was passed through the reaction mixture until all of the solvent was evaporated. Hexane (25 ml) was added and the resulting solid was broken up while heating the mixture. After cooling, filtration yielded 4 g (97.6% yield) of intermediate D as a golden solid. NMR (CDCl$_3$/DMSO-d$_6$) shows oxazine ring protons $\delta$3.5 (bs, ph—CH$_2$—N), 4.65 (s, O—CH$_2$—N), 2.4 (s, CH$_3$N).

Step 5

A mixture of intermediate D (4 g, 10.9 mmole), FeCl$_3$·6H$_2$O (4.4 g, 16.3 mmole), concentrated HCl (6 ml), water (6 ml) and methanol (30 ml) was heated at reflux overnight. Water (150 ml) was added and the mixture extracted with methylene chloride 3 times. The combined organic layers were dried (Na$_2$SO$_4$) and the solvent was removed to give 3.3 g (78.6%) of intermediate E. IR (KBr) 1660 s (quinone), 1530 s and 1430 s (NO$_2$), 2700 b (NH·HCl).

Step 6

Intermediate E (3.3 g, 8.48 mmole) was dissolved in cold methylene chloride (50 ml), and triethylamine (2.4 ml, 16.9 mmole) was added to the solution. This mixture was then added in portions over 15 minutes to a cold saturated solution of phosgene in methylene chloride (100 ml). The reaction mixture was stirred at 0° for 30 minutes, then slowly warmed to 25° over 2 hours. The mixture was held under vacuum overnight to remove all the solvent (a NaOH trap was used to collect phosgene). The resulting solid was broken up and stirred in tetrahydrofuran (250 ml). After filtration to remove the amine salt, the filtrate was freed of solvent to afford 3.3 g (94%) of intermediate F. IR (KBR) 1740 s (carbamoyl chloride), 1650 s (quinone).

Step 7

A mixture of the azo dye having the structure:

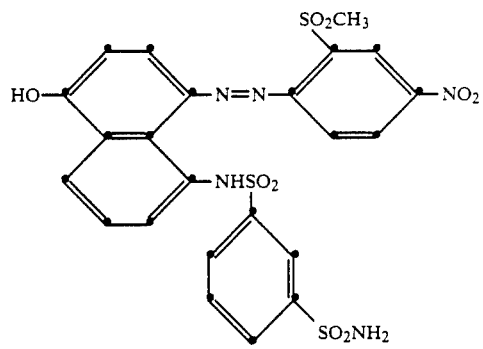

(5.3 g, 8.74 mmole), prepared from compound 6A in U.S. Pat. No. 4,199,354 (issued Aug. 22, 1980 to Hinshaw et al) by a known treatment with ammonia, and 4-piperidinopyridine (catalytic amount) was dissolved in pyridine (50 ml) in the dark under nitrogen. Intermediate F (3.3 g, 7.95 mmole), dissolved in tetrahydrofuran (5 ml), was then added and the resulting reaction mixture stirred overnight. After pouring into dilute HCl/ice water, the crude product was isolated by filtration. Column chromatography on silica (85:15, CH$_2$Cl$_2$:Et$_2$O) afforded 3 g (38%) of RIND VII. Anal. Calculated for C$_{44}$H$_{37}$N$_7$O$_{14}$S: C, 53.7, H, 3.8, N, 10.0, O, 22.8, and S, 9.8%. Found: C, 53.0, H, 3.9, N, 9.4, O, 18.6, and S, 9.2%.

EXAMPLE 2

Composition of RIND VII Compound

The RIND compound prepared in Example 1 was dissolved in N,N-dimethylformamide (16 mg per ml). An aliquot of 0.25 ml of this solution was mixed with 0.5 ml of an aqueous solution of TRITON X-100 non-ionic surfactant. The resulting solution was then added dropwise to 25 ml of 0.05 molar potassium phosphate buffer (pH 7.5) while the buffer was stirred at room temperature. A clear dispersion resulted.

EXAMPLES 3a and b

Determination of Bacterial Microorganisms with RIND XXI

*E. coli* (ATCC 25922) microorganisms were determined with RIND XXI in the following manner. A 1 ml reaction mixture was prepared with 0.5 ml of a composition of RIND XXI (prepared as described in Example 2), 10 millimolar final concentration of glucose nutrient, 0.1 millimolar final concentration of phenazine methosulfate ETA and 0.05 molar potassium phosphate buffer (pH 7.5). An aliquot of *E. coli* cell suspension (2.5 × 10$^7$ colony forming units/ml) (CFU/ml) was added to the reaction mixture and the resulting mixture was incubated at 37° C. for 10 minutes at pH 7.5. Magenta dye formation was observed as the cells reduced the RIND compound. The change in absorbance measured at 490 nm after 10 minutes is given in Table II below.

Control reaction mixtures were similarly prepared, leaving out one component of the mixture. Table II below identifies the component left out and the resulting change in absorbance ($\Delta$A) measured at 490 nm for the Controls.

TABLE II

| | ΔA at 490 nm |
|---|---|
| Example 3a | 0.149 |
| Control A - E. coli omitted | 0.008 |
| Example 3b - glucose omitted | 0.060 |
| Control B - phenazine methosulfate omitted | 0.002 |

Comparisons of Controls A and B with Examples 3a and b indicate that E. coli (a bacterial reductant) requires an electron transfer agent for efficient dye release from the RIND compound. Looking at Example 3b, the presence of a readily metabolizable substrate (i.e. glucose) is preferred in the determination of microorganisms, but without it some dye is still released.

EXAMPLE 4

Detection of Bacterial Microorganisms by Comparative Methods

This is an example comparing the detection of E. coli by the method of this invention to a prior art method using a tetrazolium salt having the structure:

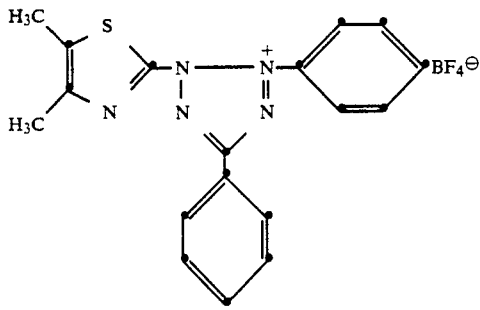

One ml reaction mixtures were prepared as described in Example 3 containing 0.5 ml of a RIND I composition and E. coli suspensions having different cell concentrations. A Control reaction mixture was prepared with the tetrazolium salt (0.2 micromoles), phenazine methosulfate (0.2 micromoles), glucose (10 micromoles) and potassium phosphate buffer (pH 7) to give a total volume of 1 ml. This mixture was equilibrated at 37° C. for 5 minutes.

The change in absorbance for each reaction mixture was measured after 10 minutes following addition of the cells to the reaction mixture. Table III below presents the data obtained. These data indicate the improved sensitivity of the RIND I compound to detect E. coli at lower cell concentrations over the tetrazolium salt.

TABLE III

| Cell Concentration E. coli (CFU/ml) | Example ΔA at 635 nm | Control ΔA at 560 nm |
|---|---|---|
| $1 \times 10^6$ | 0.014 | 0.007 |
| $5 \times 10^6$ | 0.057 | 0.031 |
| $1 \times 10^7$ | 0.103 | 0.104 |

EXAMPLE 5

Detection of Bacterial Microorganisms with Various RIND Compounds

One ml reaction mixtures of RIND V, VII, XXII and XXIII compounds were prepared by the procedure described in example 3, each containing 0.5 ml of the RIND compound and various cell concentrations of E. coli suspensions. The mixtures were incubated at 37° C. for up to 30 minutes and the dyes released by reduction of the RIND compounds by the E. coli were determined by spectrophotometrically measuring the change in absorbance (ΔA) for RIND V and VII. RINDs XXII and XXIII released fluorescent dyes which were determined by measuring net relative fluorescence with a commercial fluorometer (excitation, 372 nm and emission, 476 nm). Table IV below lists the data obtained from these measurements.

TABLE IV

| Cell Concentration CFU/ml | RIND V ΔA at 635 nm after 30 min. | RIND VII ΔA at 635 nm after 10 min. | RIND XXII Net relative fluorescence after 30 min. | RIND XXIII |
|---|---|---|---|---|
| $5 \times 10^5$ | 0.013 | NA | NA | NA |
| $1 \times 10^6$ | 0.043 | NA | 0.01 | 0.09 |
| $5 \times 10^6$ | 0.351 | NA | 0.03 | 0.22 |
| $1 \times 10^7$ | 0.729 | 0.563 | 0.075 | 0.51 |
| $5 \times 10^7$ | NA | NA | 0.79 | 1.82 |

NA = not available

EXAMPLE 6

Detection of Various Bacterial Microorganisms

One ml reaction mixtures were prepared by the procedure described in Example 3 above containing 0.5 ml of RIND I composition and each of various urinary tract infection (UTI) microorganisms at various cell concentrations as listed in Table V below. An E. coli suspension was prepared as described above. Separate suspensions of the other microorganisms in potassium phosphate buffer were prepared in a similar manner. Each reaction mixture was incubated at 37° C. for 10 minutes after which the absorbance change (ΔA) was determined at 635 nm. A Control reaction mixture was prepared without microorganisms. The results are listed in Table V below.

TABLE V

| Microorganism | Cell Concentration (CFU/ml) | ΔA at 635 nm after 10 min. |
|---|---|---|
| Escherichia coli (ATCC 25922) | $2.5 \times 10^7$ | 0.214 |
| | $5 \times 10^7$ | 0.447 |
| Staphylococcus epidermidis (ATCC 12228) | $2.5 \times 10^7$ | 0.104 |
| | $5 \times 10^7$ | 0.222 |
| Enterobacter cloacae (ATCC 23355) | $2.5 \times 10^7$ | 0.445 |
| | $5 \times 10^7$ | 0.910 |
| Staphylococcus aureus (ATCC 25923) | $2.5 \times 10^7$ | 0.062 |
| | $5 \times 10^7$ | 0.106 |
| Streptococcus faecalis (ATCC 19433) | $2.5 \times 10^7$ | 0.276 |
| | $5 \times 10^7$ | 0.714 |
| Klebsiella pneumoniae (ATCC 13883) | $2.5 \times 10^7$ | 0.290 |
| | $5 \times 10^7$ | 0.705 |
| Pseudomonas aeruginosa (ATCC 27853) | $2.5 \times 10^7$ | 0.020 |
| | $5 \times 10^7$ | 0.024 |
| Proteus vulgaris (ATCC 13315) | $2.5 \times 10^7$ | 0.820 |
| | $5 \times 10^7$ | 1.520 |
| Serratia marcescens (ATCC 8100) | $2.5 \times 10^7$ | 0.228 |
| | $5 \times 10^7$ | 0.547 |
| None (Control) | | 0.010 |

EXAMPLE 7

Measurement of Lactate Dehydrogenase Enzyme Activity

This example compares the practice of the present invention using a RIND compound to the use of a known NADH detection composition to detect the presence and amount of lactate dehydrogenase in an aqueous liquid.

A 1 ml reaction mixture was prepared containing lactic acid (10 micromoles), an aqueous composition of RIND V (0.5 ml), nicotinamide adenine dinucleotide (NAD+) (10 micromoles), phenazine methosulfate (0.1 micromoles) and potassium phosphate buffer (pH 7.5, 50 micromoles). A 1 ml Control reaction mixture was prepared containing lactic acid (10 micromoles), NAD+ (10 micromoles) and potassium phosphate buffer (pH 8, 50 micromoles).

Figure 1:
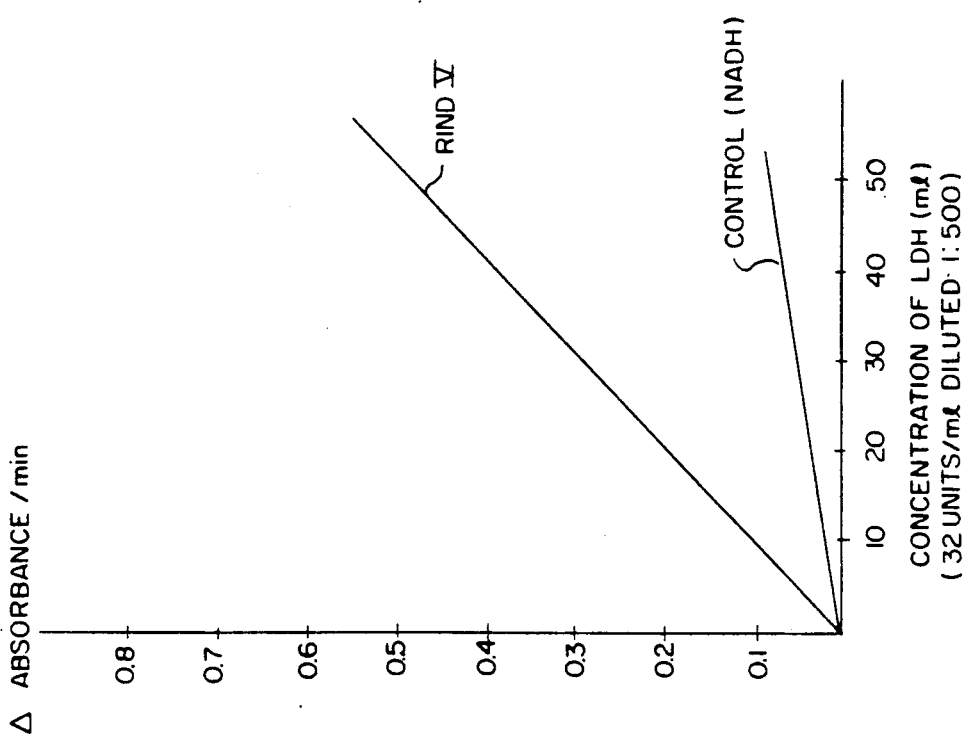
FIG. 1 is a graphical plot of the change in absorbance/min. vs. concentration of lactate dehydrogenase for both a state of the art assay and the assay of this invention in reference to Example 7 below.

Each reaction mixture was incubated at 37° C. for 5 minutes, after which lactate dehydrogenase was added. The absorbance change was monitored for each mixture with a commercial spectrophotometer at 635 nm for the RIND V mixture and at 340 nm for the Control mixture. FIG. 1 is a plot of the rate of change in absorbance for various concentrations of enzyme. This plot illustrates the significantly improved sensitivity obtained by using the RIND V compound for detection of lactate dehydrogenase (LDH) as compared to the known NAD-NADH detection composition.

EXAMPLE 8

Measurement of L-α-Glycerophosphate Oxidase Enzyme Activity

This example compares the practice of the present invention using a RIND compound to the use of a known peroxidase detection composition for the determination of L-α-glycerophosphate oxidase in an aqueous liquid.

A 1 ml reaction mixture was prepared containing D,L-α-glycerophosphate (200 micromoles), phenazine methosulfate (0.1 micromoles), an aqueous composition of RIND V (0.5 ml) and potassium phosphate buffer (pH 7, 100 micromoles). A 1 ml Control reaction mixture was prepared containing 3,3-dimethoxybenzidene dihydrochloride (66 micrograms), horseradish peroxidase (4.6 purpurogallin units, 25 micrograms), D,L-α-glycerophosphate (200 micromoles, titrated to pH 7) and potassium phosphate buffer (pH 7,100 micromoles).

Each reaction mixture was equilibrated at 37° C., after which L-α-glycerophosphate oxidase (α-GPO) was added. The absorbance change was monitored for each mixture with a commercially available spectrophotometer at 635 nm for the RIND V mixture and at 430 nm for the Control mixture. FIG. 2 is a plot of the rate of change in absorbance for various α-GPO concentrations. This plot illustrates the significantly improved sensitivity obtained using the RIND V compound for α-GPO detection as compared to the known peroxidase detection composition.

EXAMPLE 9

Measurement of Lactate Oxidase Enzyme Activity

This example compares the practice of the present invention using a RIND compound to the use of a known peroxidase detection composition for the determination of lactate oxidase in an aqueous liquid.

A 1 ml reaction mixture was prepared containing sodium L-lactate (25 micromoles), phenazine methosulfate (0.1 micromoles), an aqueous composition of RIND V (0.5 ml) and potassium phosphate buffer (pH 7.5, 100 micromoles). A 1 ml Control reaction mixture was prepared containing 3,3-dimethoxybenzidine dihydrochloride (66 micrograms), horseradish peroxidase (4.6 purpurogallin units, 25 μg), sodium L-lactate (25 micromoles) and potassium phosphate buffer (pH 7, 100 micromoles).

Figure 3:
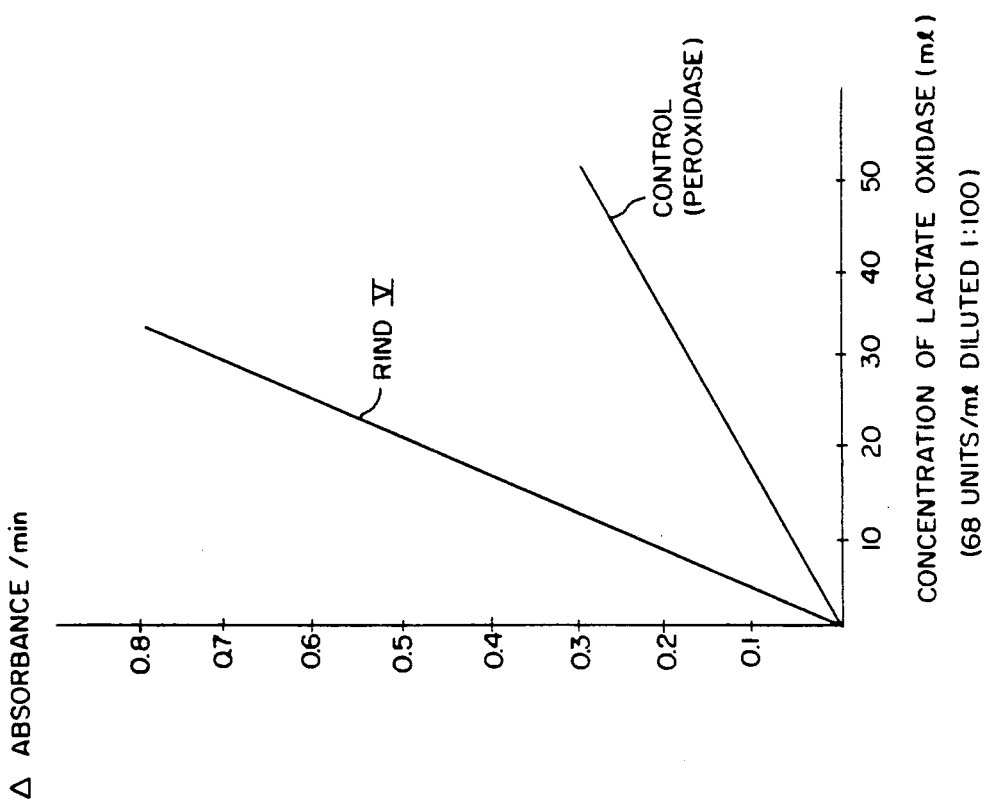
FIG. 3 is a graphical plot of the change in absorbance/min. vs. concentration of lactate oxidase for both a state of the art assay and the assay of this invention in reference to Example 9 below.

Each reaction mixture was equilibrated at 30° C., after which lactate oxidase was added. The absorbance change was monitored for each mixture with a commercially available spectrophotometer at 635 nm for the RIND V mixture and at 430 nm for the Control mixture. FIG. 3 is a plot of the rate of change of absorbance for various oxidase concentrations. This plot illustrates the significantly improved sensitivity obtained using the RIND V compound for lactate oxidase detection as compared to the Control peroxidase detection composition.

EXAMPLE 10

Measurement of Glucose Oxidase Enzyme Activity

This example is similar to Example 9. It compares the practice of the present invention using a RIND compound to the use of a known peroxidase detection composition to detect the presence and amount of glucose oxidase in an aqueous liquid.

A reaction mixture containing RIND V and a Control reaction mixture were prepared as described in Example 9 except that D-glucose (200 micromoles) was used in place of sodium L-lactate. Also, the RIND reaction mixture contained only 50 micromoles buffer (pH 7.5).

Figure 4:
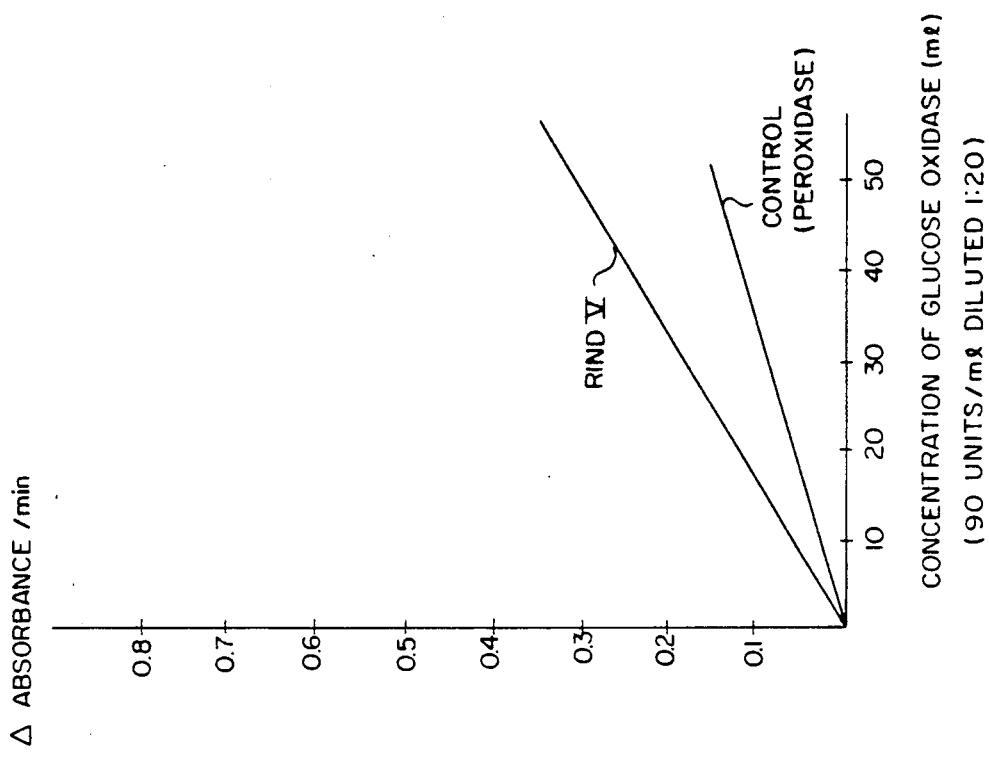
FIG. 4 is a graphical plot of the change in absorbance/min. vs. concentration of glucose oxidase for both a state of the art assay and the assay of this invention in reference to Example 10 below.

Each reaction mixture was treated as in Example 9 except glucose oxidase was added instead of lactate oxidase. FIG. 4 is a plot of the rate of change of absorbance for various glucose oxidase concentrations. This plot illustrates the significantly improved sensitivity obtained using the RIND V compound for glucose oxidase detection as compared to the known peroxidase detection composition.

EXAMPLE 11

Detection of E. coli With a Multilayer Element Containing RIND V

A multilayer analytical element was prepared having the following format and components:

| | | Range (g/m²) |
|---|---|---|
| Spreading/ Reagent Layer | Polyvinyltoluene-co-pt-butylstyrene-co-methacrylic acid) (61:37:2 weight ratio) beads (20-40 micrometers) and | 100-200 |
| | Poly(n-butyl acrylate-co-styrene-co-2-acrylamido-2-methylpropane sulfonic acid) (70:20:10 weight ratio) adhesive | 2-20 |
| | RIND V | 0.05-1 |
| | TRITON X-100 surfactant | 0.05-10 |
| Subbing Layer | Poyl(acrylamide-co-N-vinyl-2-pyrrolidone) (90:10 weight ratio) | 0.5-5 |
| | ZONYL FSN surfactant | 0.05-1 |
| | Poly(ethylene terephthalate) Support | |

Buffered (pH 7-7.5) reaction mixtures were prepared from various concentrations of E. coli cell suspensions, and 0.1 millimole phenazine methosulfate ETA, 10 millimoles glucose and enough TRITON X-100 surfactant to give a final surfactant concentration of 1%. A 10 microliter sample of this mixture was applied to the spreading/reagent layer of the above element which was then incubated at 37° C. for 10 minutes. The reflection density of the dye obtained from reduction of the RIND V compound was measured at 635 nm in a commercially available spectrophotometer, and the density change ($\Delta D_R$) was calculated as the difference between the density of a reaction mixture without cells and the density of the reaction mixture containing cells after the incubation period. Table VI below lists the $\Delta D_R$ for each test, indicating that the described element of this invention is capable of detecting various $E.\ coli$ cell concentrations. A Control test was carried out with the above described reaction mixture minus the ETA. The $\Delta D_R$ obtained was very low, indicating that the ETA is preferred for efficient dye release by $E.\ coli$.

TABLE VI

| E. coli Concentration (CFU/ml) | $\Delta D_R$ at 635 nm |
| --- | --- |
| $1 \times 10^9$ (Control) | 0.005 |
| $1 \times 10^8$ | 0.020 |
| $2.5 \times 10^8$ | 0.045 |
| $5 \times 10^8$ | 0.085 |
| $1 \times 10^9$ | 0.115 |

EXAMPLE 12

Detection of $E.\ coli$ With Multilayer Element Containing Electron Transfer Agent and RIND V A multilayer analytical element was prepared similar to that in Example 11 except that phenazine methosulfate (0.01–0.5 g/m$^2$), TRITON X-100 surfactant (1–5 g/m$^2$) and glucose nutrient (0.1–2 g/m$^2$) were incorporated into the spreading/reagent layer. A cell suspension of $E.\ coli$ ($5 \times 10^8$ CFU/ml) was prepared as described above. A 10 $\mu$l sample of the cell suspension was applied to the spreading/reagent layer of the element which was then incubated at 37° C. for 10 minutes. The reflection density, as measured by the procedure described in Example 11, was 0.073.

EXAMPLE 13

Detection of $E.\ coli$ With Multilayer Element Containing Electron Transfer Agent and RIND VII A multilayer analytical element was prepared similar to that in Example 11 except that RIND V was replaced with RIND VII (0.05–0.5 g/m$^2$) and the TRITON X-100 surfactant (2–5 g/m$^2$) and phenazine methosulfate (0.01–0.05 g/m$^2$) were incorporated into the spreading/reagent layer. A cell suspension of $E.\ coli$ ($5 \times 10^8$ CFU/ml) was mixed with 10 millimoles of glucose. A 10 $\mu$l sample of this mixture was applied to the spreading/reagent layer of the element which was then incubated at 37° C. for 10 minutes. The reflection density, as measured by the procedure described in Example 11, was 0.137.

EXAMPLE 14

Determination of Microorganisms Using Substituted Quinone Electron Transfer Agents This example, described in related U.S. Ser. No. 699,374, noted above (Example 3 therein), as noted above illustrates the use of several electron transfer agents in the practice of this invention.

Reaction mixtures were prepared with the following components: 1.5 ml of an aqueous composition of RIND IX compound prepared similarly to that described in Example 2 above, 25 $\mu$l of a solution of electron transfer agent (ETA), described below, 25 $\mu$l of a 5 wt. % glucose solution, and 0.5 ml of potassium phosphate buffer (pH 7–7.5). The electron transfer agent solutions contained phenazine methosulfate or phenazine ethosulfate in methanol (3 mg/ml), and ETAs I and III individually in methanol (1.5 mg/ml). ETAs I and III have the respective structures:

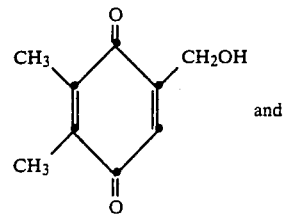

and

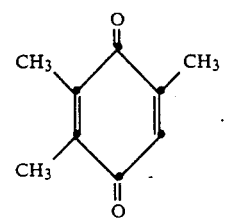

After equilibration of the reaction mixtures at 37° C., a 25 $\mu$l aliquot of the microorganism $Pseudomonas\ aeruginosa$ (ATCC 27853) (about $1 \times 10^8$ cells/ml) in a potassium phosphate buffer (pH 7.5) was added to each mixture. The release of dye from RIND IX was monitored with a commercially available Perkin-Elmer Lambda 5 spectrophotometer at 635 nm for up to 30 minutes. A Control reaction mixture without ETA was likewise monitored. Table VII below provides the $\Delta A$ (change in absorbance for the reaction mixture containing cells and the Control) observed after 15 and 30 minutes of reaction.

TABLE VII

| ETA | $\Delta A$ after 15 min. | $\Delta A$ after 30 min. |
| --- | --- | --- |
| Control | 0.092 | 0.256 |
| Phenazine ethosulfate | 0.088 | 0.237 |
| Phenazine methosulfate | 0.141 | 0.394 |
| ETA I | 0.683 | 1.921 |
| ETA III | 0.534 | 1.758 |

EXAMPLE 15

Determination of NADH in Solution Assay

This example illustrates the use of the present invention to detect nicotinamide adenine dinucleotide, reduced form (NADH) in a solution assay. The present invention can be used in the determination of an analyte during which assay NADH is either produced or eliminated.

A solution of phenazine methosulfate was prepared containing 3 mg of phenazine methosulfate in 1 ml of methanol. A stock solution of NADH was prepared containing 7.09 mg of NADH in 10 ml of water.

A dispersion of RIND IX was prepared by dissolving 4 mg of RIND IX in 250 $\mu$l of N,N-dimethylformamide, adding 0.5 ml TRITON X-100 surfactant and then adding the resulting solution slowly with stirring to 25 ml of 0.05 molar potassium phosphate buffer (pH 7.5).

A test solution was prepared from the following components: 1.5 ml RIND IX dispersion, 1.5 ml buffer and 50 $\mu$l of the NADH stock solution. Control solution 1 containing the above components plus an additional 25

μl of buffer, and omitting phenazine methosulfate, was also prepared. Control solution 2 containing the above components, except NADH, was also prepared. Twenty-five microliters of the phenazine methosulfate solution was then added to the test solution and to Control solution 2. The optical density was measured in a spectrophotometer at 635 nm at 37° C. when the solutions were first mixed and after 30 minutes. The difference in optical density for Control solution 1 was 0.002 optical units, for Control solution 2 was 0.034 optical units while the difference for the test solution was 1.124 optical units.

EXAMPLE 16

Determination of Ascorbic Acid in Solution with a RIND Compound

A stock solution of ascorbic acid, sodium salt was prepared with 1 mg of sodium ascorbate in 1 ml of water. A test solution was prepared from the following components: 1.5 ml RIND IX dispersion prepared in Example 15, 1.5 ml buffer and 100 μl of ascorbate stock solution. A Control solution containing the above components plus an additional 25 μl of buffer, but without phenazine methosulfate, was also prepared. Control solution 2 containing the above components, except ascorbic acid, was also prepared. Twenty-five microliters of phenazine methosulfate solution from Example 15, was then added to the test solution and to Control solution 2. The optical density was measured in a spectrophotometer at 635 nm and 37° C. when the solutions were first mixed and after 30 minutes. The difference in optical density for Control solution 1 was 0.121 optical units, for Control solution 2 was 0.034 optical units and for the test solution was 1.232 optical units. These data indicate that ascorbic acid (or its equivalent salt) can be determined using a RIND compound.

EXAMPLE 17

Preparation of RIND Compound Containing An Enzyme Inhibitor

The following compound was prepared:

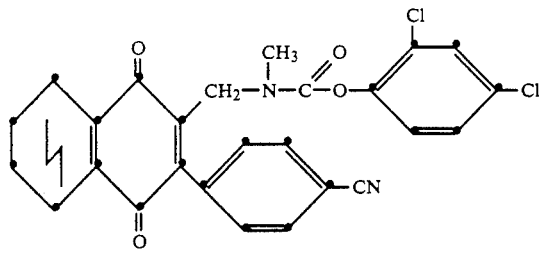

An intermediate carbamoyl chloride was prepared according to the procedure of Steps 1-6 of Example 1 above except p-cyanoaniline was used in place of p-nitroaniline. This intermediate (5 g, 12.6 mmole) was added to a solution of 2,4-dichlorophenol (1.72 g, 10.6 mmole), which is a known inhibitor of catalase, and dimethylaminopyridine (catalytic amount) in pyridine (30 ml). The resulting mixture was stirred under a nitrogen atmosphere while protected from light for 18 hours. The reaction mixture was then poured into a dilute hydrochloric acid/ice water mixture (1 liter), and the solid obtained was collected by filtration, washed with water and air dried. Chromatography (silica, methylene chloride:ether/95:5) followed by recrystallization from ethanol provided 4.65 g (84% yield) of the desired RIND compound which had a m.p. of 150°-152° C. Mass spectral and nuclear magnetic resonance analyses confirmed the structure shown above. Calculated elemental analysis for $C_{28}H_{22}Cl_2N_2O_4$ was: C, 64.5, H, 4.3, Cl, 13.6, N, 5.4. Found: C, 64.5, H, 4.4, Cl, 13.0, N, 5.1.

EXAMPLE 18

Release of Enzyme Inhibitor from RIND Compound

The release of the catalase inhibitor 2,4-dichlorophenol from the RIND compound prepared in Example 17 above was determined using high performance liquid chromatography. The apparatus used consisted of a Model 710B autoinjector (Water Associates, Milford, Mass.), two solvent delivery pumps, Model 6000, controlled by a 720 system controller (Water Associates), a photodiode array detector (Model 1040A, Hewlett-Packard, Palo Alto, Calif.), integrator (LAS System, Model 3357, Hewlett-Packard), and a Zorbax $C_{18}$ column (DuPont Co. Wilmington, Del.). The solvent system used was a mixture of acetonitrile and 0.5% phosphoric acid (3:2). The flow rate was 1 ml/minute.

The RIND compound of Example 17 was dissolved in a 7% solution of 1:1 BRIJ 35 surfactant/N,N-dimethylformamide in water to obtain a solution having a concentration of $1.7 \times 10^{-4}$ molar. Trimethylhydroquinone was used as the reductant. It was dissolved in a 7% solution of 1:1 BRIJ 35 surfactant/N,N-dimethylformamide in potassium phosphate buffer (0.05 molar, pH 7.5) to obtain a solution having a concentration of 0.02 molar. These solutions were mixed and automatically injected into the chromatography apparatus described above.

Rapid reduction of the RIND compound was observed. Then a single peak having a retention time of 6.8 minutes was detected at two wavelengths (254 nm and 280 nm). The peak was a composite of the peaks from the two products of the reaction, an oxazine product resulting from the RIND compound after release of the inhibitor, and the inhibitor 2,4-dichlorophenol.

EXAMPLE 19

Preparation and Use of a Nitrobenzenoid RIND Compound to Determine E. coli Cells The following compound was prepared:

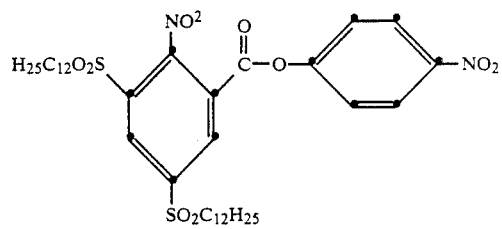

An intermediate acid chloride (5 g, 7.7 mmole) was prepared as described in U.S. Pat. No. 4,139,379, and dissolved in tetrahydrofuran (50 ml). The sodium salt of p-nitrophenol (1.67 g, 8.5 mmole) was added to the solution. After stirring at room temperature for 1.5 hours, the reaction mixture was poured into dilute hydrochloric acid and ice water (500 ml). The resulting white solid was isolated by filtration, washed with water and air dried. Column chromatography (silica, dichloromethane) provided a white solid which was washed with ethanol, filtered and dried to give 2.8 g (48%) of the desired product having a m.p. of 147°-149°

C. The nuclear magnetic resonance spectrum confirmed the structure shown above. The calculated elemental analysis for $C_{37}H_{56}N_2O_{16}S_2$ was: C, 59, H, 7.5, N, 3.7, S, 8.5. Found: C, 59.2, H, 7.4, N, 3.6, S, 8.0

An assay for the microorganism *E. coli* was performed using the RIND compound prepared above in the following manner.

A solution of the RIND compound was prepared by dissolving the RIND compound (6 mg, $8 \times 10^{-6}$ mole) in 0.5 ml N,N-dimethylformamide which had been acidified with 0.1% sulfuric acid. TRITON X-100 surfactant (0.5 ml) was added and the resulting solution was added to 25 ml of potassium phosphate buffer (0.05 molar, pH 7.8).

A test solution was prepared from the following: 1.5 ml RIND compound solution, 25 μl ETA solution (1.5 mg trimethyl-1,4-benzoquinone per ml methanol), 25 μl of 10% glucose solution and 0.3 ml of *E. coli* cells in phosphate buffer (final concentration $5 \times 10^7$ CFU/ml). A Control solution was prepared without the cells. Solutions were made up to equal volumes using phosphate buffer. Transmission densities were measured at 410 nm when the solutions were first mixed (about 2 minutes) and after incubation at 37° C. for 30 minutes. The change in density for the Control was 0.114 units. The change in density for the test solution, after subtracting the background density of the Control, was 0.329 units.

EXAMPLE 20

Preparation of Quinonemethide Reducible Compound and Its Use to Determine *E. coli* Cells The following compound was prepared:

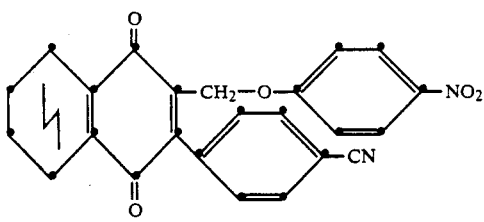

A quinone carrier was prepared by a standard oxidation of the corresponding hydroquinone which had been prepared according to the procedure describe in Steps 1-3 of Example 1 above using p-cyanoaniline in place of p-nitroaniline. This material (5.2 g, 18 mmole) was added to a mixture of hydrobromic acid (30% in acetic acid, 48 ml), 37% formalin (18 ml) and acetic acid (140 ml), and the resulting solution was heated at 55° C. for 18 hours. After cooling, the reaction mixture was poured into ice water (500 ml) and the resulting yellow solid was recrystallized from ethanol to give 2.4 g of the bromomethyl intermediate having a m.p. of 201°-202° C. An NMR spectrum confirmed the structure.

This intermediate (5.25 g, 14 mmole) in tetrahydrofuran (100 ml) was treated with the sodium salt of p-nitrophenol (3.5 g, 18 mmole), and the reaction mixture was stirred under a nitrogen atmosphere, protected from light, for 8 hours. The mixture was then poured into dilute hydrochloric acid and ice water (800 ml) and extracted with dichloromethane. The extracts were combined and dried, and the solvent was removed. The crude product was chromatographed (silica, dichloromethane), and the resulting material was recrystallized from ethanol to give 3.1 g of the desired reducible compound as a yellow solid having a m.p. of 191°-196° C.

The NMR spectrum confirmed the structure shown above. Elemental analysis calculated for $C_{26}H_{20}N_2O_5$ was: C, 70.9, H, 4.6, N, 6.4. Found: C, 70.5, H, 4.7, N, 6.3.

A solution of the reducible compound shown above (3.5 mg) was prepared in N,N-dimethylformamide (250 μl) which had been acidified with 0.1% sulfuric acid. TRITON X-100 surfactant (0.5 ml) was added, and the resulting solution was added to 25 ml of potassium phosphate buffer (0.05 molar, pH 7.8).

Test solutions were prepared from 1.5 ml reducible compound solution, 25 μl of ETA solution (1.5 mg trimethyl-1,4-benzoquinone/ml methanol), 25 μl 10% glucose solution and two cell concentrations of *E. coli*, 0.3 ml (final cell concentration of $5 \times 10^7$ CFU/ml) and 60 μl (final cell concentration of $1 \times 10^7$ CFU/ml). Control solutions were prepared without *E. coli* cells. The solutions were made up to equal volume with potassium phosphate buffer. Transmission densities were then measured at 410 nm both when the solutions were first mixed (after 2 minutes) and then after 30 minutes at 37° C. The density changes resulting from these determinations are presented in Table VIII below.

TABLE VIII

| Cell Concentration (CFU/ml) | Change in Density (410 nm after 28 minutes) | |
|---|---|---|
| | Control | Test (Minus Control) |
| $5 \times 10^7$ | 0.017 | 1.23 |
| $1 \times 10^7$ | 0.018 | 0.297 |

EXAMPLE 21

Preparation of RIND XXIX and Buffered Composition Containing Same

Step A

A mixture of p-cyanoaniline (23.5 g, 0.2 mole), concentrated HCl (80 ml) and water (200 ml) was warmed until solution was obtained, then cooled to 0°-5° C. Sodium nitrite (13.8 g, 0.2 mole), dissolved in $H_2O$ (25 ml), was added slowly to prevent any rise in temperature. After stirring at 0° C. for one hour, the resulting diazonium salt was added slowly to a mechanically stirred mixture of p-benzoquinone (25.9 g, 0.23 mole), sodium acetate (100 g, 1.2 mole), and ice water (2300 ml). The mixture was stirred in an ice bath for four hours and slowly warmed to room temperature. The solid was isolated by filtration, washed repeatedly with water, then dried and recrystallized from acetonitrile to give 21.7 g of Intermediate A.

Steps B-F

Intermediate A was then treated according to the procedure described in Example 1, Steps 2a-6 noted above.

Step G

Intermediate F (17.3 g, 43.7 mmole) was added in portions over 45 minutes to a solution of 6-hydroxyphenalenone (6.6 g, 33.6 mmole) and 4-dimethylaminopyridine (catalytic amount) in pyridine (175 ml). The reaction mixture was stirred at 25° C. for 15 hours under a nitrogen atmosphere. The resulting mixture was poured into hydrochloric acid and ice water (3 liters) to precipitate a yellow solid. The solid was collected by filtration, washed with water and dried under vacuum. Chromatography (silica, 90:10, dichloromethane:acetone) gave a yellow foam which was solidified by stirring for 15 minutes in ether (100 ml). The solid was collected and dried to give 13.8 g (74% yield) of RIND XXIX, m.p. 210°–213° C. Analysis, calculated for $C_{35}H_{26}N_2O_5$: C, 75.8, H, 4.7, N, 5.1. Found: C, 75.1, H, 4.9, N, 5.0.

Step H

A buffered dispersion of the RIND XXIX compound was prepared as follows: RIND XXIX was dissolved in N,N-dimethylformamide (16 mg per ml). An aliquot of 0.25 ml of this solution was mixed with a solution of TRITON X-100 nonionic surfactant. The resulting solution was then added dropwise to 25 ml of 0.05 molar potassium phosphate buffer (pH 7.5) while stirred at room temperature. A clear dispersion resulted.

EXAMPLE 22

Preparation of RIND XXX and Buffered Composition Containing Same

RIND XXX was prepared with the following sequence of steps.

Step A

A mixture of 2,5-dimethoxy-4-phenylbenzaldehyde (52.5 g, 0.22 mole), malonic acid (51.8 g, 0.5 mole), and piperidine (2.5 ml) in pyridine (100 ml) was heated at 80° C. for 15 hours. After cooling, the mixture was poured into hydrochloric acid/ice water (2.5 liters). The precipitated yellow solid was collected by filtration, washed with water, and dried on the filter. The product was refluxed in acetonitrile (600 ml) for 30 minutes, the mixture was cooled, and the yellow solid was collected, washed with acetonitrile, and dried on the filter. This product (43.3 g) was suspended in ethanol (1.25 liter), placed in a Parr shaker bottle with 10% Palladium on charcoal catalyst and shaken under hydrogen for 3 days. The catalyst was filtered off, and the filtrate was concentrated to yield 35 g of Intermediate A having a m.p. of 143°–146° C.

Step B

A mixture of Intermediate A (35 g, 0.12 mole) and oxalyl chloride (23.3 g, 0.18 mole) in dichloromethane (400 ml) was stirred at 25° C. for 8 hours. The solution was concentrated under reduced pressure to yield an orange oil. Two separate portions of dichloromethane (about 50 ml) were added and then removed under reduced pressure. The oil obtained (about 37 g, Intermediate B) was used directly in the next step.

Step C

Intermediate B (about 37 g, 0.12 mole) was dissolved in dichloromethane (400 ml). This solution was cooled in an ice bath and stannic chloride (38 g, 0.15 mole) was added. The reaction mixture was allowed to set at 25° C. for 30 hours, then poured into hydrochloric acid/ice water (3 liters) and stirred for 15 minutes. The layers were separated, and the water layer was washed twice with dichloromethane. The organic layers were combined, dried, and concentrated under reduced pressure to give a solid product. Chromatography on silica with dichloromethane, ether (98:2) gave 28 g of yellow Intermediate C, having a m.p. of 97°–99° C.

Step D

A solution of Intermediate C (28 g, 0.104 mole) in acetic acid (600 ml) and perchloric acid (12 ml) was placed in a Parr shaker bottle with 10% Palladium on charcoal catalyst and shaken under hydrogen for one week. Potassium acetate (about 10 g) was added, and the mixture was stirred for 10 minutes, and filtered to remove the catalyst. The filtrate was concentrated under reduced pressure to give a semi-solid product. This product was dissolved in tetrahydrofuran and the solution was poured into ice water. The water was extracted with dichloromethane and the solvent was dried and concentrated. Toluene was added in two separate portions and removed under reduced pressure. There was obtained 23.5 g of Intermediate D.

Step E

Cerric ammonium nitrate (152 g, 0.28 mole) was dissolved in water (325 ml) and added dropwise with stirring over 45 minutes to a solution of Intermediate D in acetonitrile (325 ml). The reaction mixture was allowed to stir and additional 30 minutes. Water (300 ml) was added, and the mixture was extracted with dichloromethane (4×100 ml) and ethyl ether (1×100 ml). The organic layers were combined, dried, and concentrated to yield 24 g of orange oil. A purified sample of the oil solidified having a m.p. of 81°–82.5° C.

Step F

Intermediate E (24 g, 0.11 mole) was dissolved in tetrahydrofuran (200 ml), placed in a Parr shaker bottle with 10% Palladium on charcoal, and shaken under hydrogen for 75 minutes. The catalyst was filtered off under nitrogen, and the filtrate was concentrated to give 23 g of Intermediate F. This product was used directly in the next reaction.

Step G

Intermediate F (23 g, 0.1 mole) and N,N-(diisobutoxymethylene)methylamine (30.9 g, 0.15 mole) in toluene (50 ml) were heated at 90° C. under a nitrogen atmosphere for 3 hours. Thin layer chromatography (silica, dichloromethane:ether, 95:5) showed the presence of starting material. The solvent was removed, N,N-(diisobutoxymethylene)methylamine (1 ml) was added, and the mixture was heated neat for an additional 3 hours. Methanol (50 ml) was added and the mixture was brought to reflux. The mixture was allowed to cool overnight at 0° C. The product was collected, washed with cold methanol, and dried. There was obtained 11.9 g of Intermediate G, having a m.p. of 212°–213° C.

Step H

A mixture of intermediate G (11.9 g, 0.04 mole) and ferric chloride (17.1 g, 0.063 mole) in hydrochloric acid (35 ml), water (35 ml), and methanol (100 ml) was refluxed for 8 hours. The reaction mixture was cooled at 0° C. for several hours and filtered. The filtrate was treated with water (100 ml) and extracted with tetrahydrofuran/dichloromethane (1:1) 3 times with 100 ml. The combined extracts were dried, treated with charcoal, and filtered. The filtrate was concentrated to yield 10.3 g of Intermediate H.

Step I

Intermediate H (10.3 g, 0.034 mole) and triethylamine (6.9 g, 0.068 mole) were dissolved in dichloromethane (100 ml). This solution was added in portions at 0° C. with stirring to dichloromethane (300 ml), which had previously been saturated with phosgene gas. The reaction mixture was allowed to stir at 0° C. for 15 minutes followed by warming to 25° C. over two hours. The solvent was removed under reduced pressure and ethyl ether/tetrahydrofuran (1:1, 100 ml) was added. This mixture was stirred, and the solid was filtered off and washed with ethyl ether/tetrahydrofuran. The filtrate was concentrated to give 11.1 g of Intermediate I.

Step J

A suspension of 6-hydroxyphenalenone (2.4 g, 0.013 mole) in pyridine (100 ml) under a nitrogen atmosphere was treated with a catalytic amount of 4-N,N-dimethylaminopyridine and Intermediate I (5 g, 0.015 mole), then stirred in a dark area for 5 hours. The reaction mixture was poured into hydrochloric acid/ice water (2 liters), the solid product was collected, washed with water, and dried under vaccum for 15 hours in a dark area. Chromatography (silica, dichloromethane/acetone, 9:1) yielded 1.3 g of product, RIND XXX. Analysis: calculated for $C_{31}H_{23}NO_5$: C, 76.1, H, 4.7, N, 2.9. Found: C, 74.1, H, 4.8, N, 2.8.

A dispersion of RIND XXX was prepared by the same procedure described in Example 21.

EXAMPLE 23

Solution Assay for *Pseudomonas aeruginosa* Using RIND XXX

The following solutions were used in this assay: an electron transfer agent (ETA) in methanol, 0.01 molar, and *Pseudomonas aeruginosa*, grown in brain heat infusion medium and having a concentration of $1 \times 10^8$ cells/ml.

Solutions were prepared from the following components: 1.5 ml RIND XXX dispersion prepared as described in Example 21, 1.5 ml potassium phosphate buffer (pH 7.5), 25 μl glucose stock solution (10%) and 25 μl of *Pseudomonas aeruginosa* solution. Twenty-five μl of the appropriate ETA were then added. A Control did not contain any ETA. The fluorescence was then measured at 25° C. in a commercial Farrand spectrofluorometer (excitation, 540 nm, emission, 620 nm) at initial time (when solutions were first mixed) and at 5, 15, and 30 minutes later.

The results, shown in Table IX below, indicate that RIND XXX can be used in a solution assay for *Pseudomonas aeruginosa* using two different electron transfer agents.

TABLE IX

| Solution | Relative Fluorescence | | | |
|---|---|---|---|---|
| | Initial Time | 5 Min | 15 Min | 30 Min |
| Control | 0.058 | 0.062 | 0.066 | 0.078 |
| TMBQ* | 0.059 | 0.081 | 0.144 | 0.290 |
| DMHBQ** | 0.058 | 0.087 | 0.177 | 0.360 |

*2,3,5-Trimethyl-1,4-benzoquinone
**2,3-Dimethyl-5-hydroxymethyl-1,4-benzoquinone

EXAMPLE 24

Solution Assay for Nicotinamide Adenine Dinucleotide, Reduced Form and Ascorbate Using RIND XXIX This example demonstrates the use of RIND XXIX to assay for the biological reductants nicotinamide adenine dinucleotide, reduced form (NADH), and ascorbic acid.

Stock solutions of the following reagents were used: NADH (7.09 mg) in 10 ml distilled water, and sodium ascorbate (1.98 mg) in 10 ml distilled water.

A dispersion of RIND XXIX was prepared by dissolving 4 mg of RIND XXIX in 250 μl of N,N-dimethylformamide, adding 0.5 ml of TRITON X-100 surfactant and then adding this solution slowly with stirring to 25 ml of 0.05 molar potassium phosphate buffer.

Test solutions were prepared from the following components: 1.5 ml RIND XXIX dispersion, 1.5 ml of 0.05 molar potassium phosphate buffer (pH 7.5) and 25 μl phenazine methosulfate solution (3 mg/ml methanol). Varying concentrations of the reductants, as shown in the tables, were added to these solutions. The fluorescence was then measured at 25° C. after 5 minutes (excitation, 540 nm and emission, 620 nm) for each reductant series, which included a Control where reductant was absent. The results, listed in Tables X and XI below, indicate that RIND XXIX is useful in determinations of NADH and ascorbate, respectively.

TABLE X

Assay for NADH

| NADH Concentration | Relative Fluorescence (5 Min.) |
|---|---|
| Control | 0.042 |
| $3.3 \times 10^{-8}$ molar | 0.046 |
| $3.3 \times 10^{-7}$ molar | 0.043 |
| $3.3 \times 10^{-6}$ molar | 0.096 |
| $3.3 \times 10^{-5}$ molar | 0.370 |

TABLE XI

Assay for Ascorbic Acid

| NADH Concentration | Relative Fluorescence (5 Min.) |
|---|---|
| Control | 0.044 |
| $3.3 \times 10^{-8}$ molar | 0.049 |
| $3.3 \times 10^{-7}$ molar | 0.049 |
| $3.3 \times 10^{-6}$ molar | 0.096 |
| $3.3 \times 10^{-5}$ molar | 0.450 |

EXAMPLE 25

Detection of *E. coli* with RIND XXIX in a Dry Element

A dry element having the following format was used in this example.

| | | |
|---|---|---|
| Spreading/ Reagent Layer | Poly(vinyltoluene-co-p-t-butylstyrene-co-methacrylic acid) Beads | 100–150 g/m² |
| | Poly(n-butyl acrylate-co-styrene-co-2-acrylamido-2-methylpropane sulfonic acid, sodium salt) | 2–6 g/m² |
| | TRITON X-100 surfactant | 2–5 g/m² |
| | Glucose | 0.1–0.5 g/m² |
| | RIND XXIX | 0.1–0.5 g/m² |
| | 2,3,5-Trimethyl-1,4-benzoquinone | 0.8–4 g/m² |
| Reflection Layer | Gelatin (hardened) | 1–10 g/m² |
| | Titanium dioxide | 0.5–5.0 g/m² |
| | ZONYL FSN surfactant | 0.1–0.5 g/m² |
| | DAXAD 30 surfactant | 0.02–0.04 g/m² |
| Mordant/ Registration Layer | Gelatin (hardened) | 1–10 g/m² |
| | Poly(styrene-co-N-vinylbenzyl-N,N-dimethylbenzylammonium chloride-co-divinylbenzene) mordant | 0.05–5.0 g/m² |
| | ZONYL FSN surfactant | 0.1–0.5 g/m² |

-continued

Poly(ethylene terephthalate)
Support

To evaluate this element, solutions of varying *E. coli* cell concentrations in potassium phosphate buffer (pH 7.5) and a Control containing only buffer were prepared. These solutions were then spotted onto the element using 10 μl drops, and the element was incubated at 37° C. for up to 60 minutes. The fluorescence was measured in a modified, commercial fluorometer (excitation, 540 nm, emission, 620 nm) after 3 minutes and at 60 minutes in the incubation period. The results, listed in Table XII below, show the difference in relative fluorescence at 3 and 60 minutes and indicate that approximately $10^7$ cells/ml can be detected using this element.

TABLE XII

| E. coli (Cells/ml) | Relative Fluorescence 57 Min., 37° C. | Standard Deviation | CV (%)* |
|---|---|---|---|
| $1.0 \times 10^7$ | 0.272 | 0.007 | 2.6 |
| $4.1 \times 10^6$ | 0.249 | 0.007 | 2.8 |
| 0 | 0.221 | 0.010 | 4.5 |

*CV = Coefficient of Variation

The present invention has been described in detail with particular reference to preferred embodiments thereof, but it will be understood that variations and modifications can be effected within the spirit and scope of the invention.

We claim:

1. A method for the determination of an analyte comprising the steps of:
   A. at a pH of 9 or less, contacting a sample of a liquid suspected of containing an analyte with a reducible compound of the structure CAR$-(R^1)_n$ wherein CAR— is a substituted or unsubstituted aromatic or quinone nucleus, $R^1$ is a moiety which comprises a shiftable detectable species, and n is 1 or 2,
   provided said compound is capable of being reduced at said pH to release said shiftable detectable species, and
   further provided that when $R^1$ is replaced with H, CAR$-(H)_n$ has an $E_{\frac{1}{2}}$ of either at least about +100 mV when measured in water, or of at least about −650 mV when measured in acetonitrile, and
   B. detecting the detectable species released as a result of the presence of said analyte.

2. The method of claim 1 wherein said detectable species is a chromogen or fluorogen.

3. A method for the determination of an analyte comprising the steps of:
   A. at a pH of 9 or less, contacting a sample of a liquid suspected of containing an analyte with a reducible compound of the structure CAR—$R^1$ wherein CAR— is

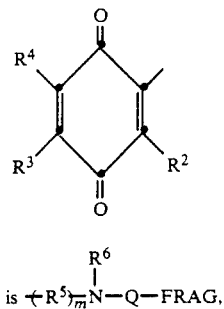

$R^1$ is $-(R^5)_m-N-Q-FRAG$, $R^2$ and $R^4$ are independently hydrogen, substituted or unsubstituted alkyl, substituted or unsubstituted aryl or an electron withdrawing group, $R^3$ is $R^1$, hydrogen, substituted or unsubstituted alkyl, substituted or unsubstituted aryl or an electron withdrawing group, or $R^3$ and $R^4$, taken together, represent the atoms necessary to complete a substituted or unsubstituted fused carbocyclic ring, $R^5$ is substituted or unsubstituted alkylene of 1 or 2 carbon atoms, $R^6$ is substituted or unsubstituted alkyl, substituted or unsubstituted cycloalkyl, substituted or unsubstituted heterocycle or substituted or unsubstituted aryl, provided that when FRAG is a fluorogen, $R^6$ is methyl, Q is carbonyl or thiocarbonyl, FRAG is a shiftable detectable species which provides a detectable species when released from said reducible compound, and m is 0 or 1, provided that when $R^1$ is replaced with H, CAR—H has an $E_{\frac{1}{2}}$ of either at least about +100 mV when measured in water, or of at least about −650 mV when measured in acetonitrile, and B. detecting the detectable species released as a result of the presence of said analyte.

4. The method of claim 3 for the determination of a nonliving analyte in the presence of an interactive composition for said analyte.

5. The method of claim 3 for the determination of living cells in the presence of an electron transfer agent.

6. The method of claim 5 for the determination of bacterial cells.

7. The method of claim 5 wherein when said compound is reduced at about pH 7, at least about 50% of said FRAG moiety is released within about 30 minutes.

8. A method for providing a chemically or biologically useful moiety comprising, at a pH of 9 or less, reducing a reducible compound of the structure CAR$-(R^1)_n$ wherein CAR— is a substituted or unsubstituted aromatic or quinone nucleus, $R^1$ is a moiety which comprises a shiftable detectable species, and n is 1 or 2,
   provided said compound is capable of being reduced at said pH to release said shiftable detectable species, and
   further provided that when $R^1$ is replaced with H, CAR$-(H)_n$ has an $E_{\frac{1}{2}}$ of either at least about +100 mV when measured in water, or at least about −650 mV when measured in acetonitrile.

* * * * *